(12) United States Patent
Podolski et al.

(10) Patent No.: US 9,687,458 B2
(45) Date of Patent: Jun. 27, 2017

(54) TRANS-CLOMIPHENE FOR USE IN CANCER THERAPY

(71) Applicant: REPROS THERAPEUTICS INC., The Woodlands, TX (US)

(72) Inventors: Joseph S. Podolski, The Woodlands, TX (US); Ronald D. Wiehle, Houston, TX (US); Kuang Hsu, The Woodlands, TX (US); Greg Fontenot, The Woodlands, TX (US)

(73) Assignee: Repros Therapeutics Inc., The Woodlands, TX (US)

(*) Notice: Subject to any disclaimer, the term of this patent is extended or adjusted under 35 U.S.C. 154(b) by 0 days.

(21) Appl. No.: 14/440,007

(22) PCT Filed: Oct. 22, 2013

(86) PCT No.: PCT/US2013/066141
§ 371 (c)(1),
(2) Date: Apr. 30, 2015

(87) PCT Pub. No.: WO2014/070523
PCT Pub. Date: May 8, 2014

(65) Prior Publication Data
US 2015/0283099 A1    Oct. 8, 2015

Related U.S. Application Data

(60) Provisional application No. 61/722,013, filed on Nov. 2, 2012.

(51) Int. Cl.
*A61K 31/138* (2006.01)
*A61K 45/06* (2006.01)
*A61K 31/155* (2006.01)

(52) U.S. Cl.
CPC .......... *A61K 31/138* (2013.01); *A61K 31/155* (2013.01); *A61K 45/06* (2013.01)

(58) Field of Classification Search
None
See application file for complete search history.

(56) References Cited

U.S. PATENT DOCUMENTS

| | | |
|---|---|---|
| 2,914,563 A | 11/1959 | Allen et al. |
| 3,848,030 A | 11/1974 | Viterbo et al. |
| 4,061,733 A | 12/1977 | Gunjikar |
| 4,729,999 A | 3/1988 | Young |
| 4,820,736 A | 4/1989 | Jensen et al. |
| 4,894,373 A | 1/1990 | Young |
| 5,681,863 A | 10/1997 | Bitonti et al. |
| 5,728,688 A | 3/1998 | Labrie |
| 5,861,389 A | 1/1999 | Radlmaier |
| 6,017,964 A | 1/2000 | MacLean et al. |
| 6,096,338 A | 8/2000 | Lacy |
| 6,126,969 A | 10/2000 | Shah |
| 6,129,933 A | 10/2000 | Oshlack |
| 6,143,353 A | 11/2000 | Oshlack |
| 6,190,591 B1 | 2/2001 | Van Lengerich |
| 6,221,399 B1 | 4/2001 | Rolfes |
| 6,248,363 B1 | 6/2001 | Patel |
| 6,291,505 B1 | 9/2001 | Huebner et al. |
| 6,342,250 B1 | 1/2002 | Masters |
| 6,391,920 B1 | 5/2002 | Fisch |
| 6,511,986 B2 | 1/2003 | Zhang et al. |
| 6,583,129 B1 | 6/2003 | Mazer et al. |
| 6,600,010 B2 | 7/2003 | Mao et al. |
| 6,638,528 B1 | 10/2003 | Kanios |
| 6,645,974 B2 | 11/2003 | Hutchinson et al. |
| 6,653,297 B1 | 11/2003 | Hodgen |
| 6,685,957 B1 | 2/2004 | Bezemer et al. |
| 6,743,448 B2 | 6/2004 | Kryger |
| 7,067,557 B2 | 6/2006 | Fisch |
| 7,105,679 B2 | 9/2006 | Kanojia et al. |
| 7,354,581 B2 | 4/2008 | Cedarbaum et al. |
| 7,799,782 B2 | 9/2010 | Munson et al. |
| 8,247,456 B2 | 8/2012 | Podolski |
| 8,377,991 B2 | 2/2013 | Van As |
| 2002/0120012 A1 | 8/2002 | Fisch |

(Continued)

FOREIGN PATENT DOCUMENTS

| | | |
|---|---|---|
| AU | 2001261684 | 12/2001 |
| CN | 103351304 A | 10/2013 |

(Continued)

OTHER PUBLICATIONS

Kaaks, R., "Nutrition, insulin, IGF-1 metabolism and cancer risk: a summary of epidemiological evidence", 2004, Biology of IGF-1: Its Interaction with Insulin in Health and Malignant States, vol. 262, Wiley, Chichester (Novartis Foundation Symposium 262), pp. 247-264.*
Dunn et al., "Insulin-like Growth Factor 1 (IGF-1) Alters Drug Sensitivity of HBL100 Human Breast Cancer Cells by Inhibition of Apoptosis Induced by Diverse Anticancer Drugs", Cancer Research, 1997, vol. 57, pp. 2687-2693.*
Heidegger et al., "Targeting the insulin like growth factor network in cancer therapy", Cancer Biology & Therapy, Apr. 2011, vol. 11(8), pp. 701-707.*
Bitonti, A. J., et al., "Antiproliferative Activity of Enclomiphene and Analogs with Extended Diethylaminoalkoxy Sidechains Against Human Breast Cancer Cells in Vitro and Human Tumor Xenografts in Nude Mice," Proceedings of the Annual Meeting of the American Association for Cancer Research, vol. 35, pp. 267 (Apr. 13, 1994).

(Continued)

*Primary Examiner* — Savitha Rao
*Assistant Examiner* — Gregg Polansky
(74) *Attorney, Agent, or Firm* — Morgan, Lewis & Bockius, LLP.

(57) ABSTRACT

The present invention relates to the administration of compositions comprising an antiestrogen, preferably a selective estrogen receptor modulator (SERM) such as trans-clomiphene, for treating cancer and associated diseases. The invention is also directed to methods for reducing IGF-1 levels in a subject in need thereof by administering a composition comprising an antiestrogen, preferably a SERM such as trans-clomiphene.

18 Claims, 10 Drawing Sheets

(56) References Cited

U.S. PATENT DOCUMENTS

| | | |
|---|---|---|
| 2002/0183296 A1 | 12/2002 | Dudley et al. |
| 2003/0040510 A1 | 2/2003 | Labrie |
| 2004/0097597 A1 | 5/2004 | Podolski et al. |
| 2004/0171697 A1 | 9/2004 | Podolski et al. |
| 2004/0220154 A1 | 11/2004 | Kryger |
| 2004/0241224 A1 | 12/2004 | Podolski et al. |
| 2005/0042268 A1 | 2/2005 | Aschkenasy et al. |
| 2005/0171073 A1 | 8/2005 | Steiner et al. |
| 2006/0269611 A1 | 11/2006 | Steiner et al. |
| 2006/0293294 A1 | 12/2006 | Blom et al. |
| 2007/0004626 A1 | 1/2007 | Masuda et al. |
| 2007/0101166 A1 | 5/2007 | Boyum et al. |
| 2007/0202166 A1 | 8/2007 | Heuer et al. |
| 2009/0036415 A1 | 2/2009 | Rubin et al. |
| 2009/0099265 A1 | 4/2009 | Van As |
| 2009/0215906 A1 | 8/2009 | Podolski |
| 2010/0054248 A1 | 3/2010 | Fernandez Gutierrez |
| 2010/0111901 A1 | 5/2010 | Gant et al. |
| 2010/0144687 A1 | 6/2010 | Glaser |

FOREIGN PATENT DOCUMENTS

| | | |
|---|---|---|
| EP | 0206021 A | 8/1988 |
| EP | 0888775 A2 | 7/1999 |
| EP | 1090639 A2 | 4/2001 |
| EP | 1829534 A1 | 3/2006 |
| WO | WO 95/35093 | 12/1995 |
| WO | WO 00/05954 | 2/2000 |
| WO | WO 01/34117 A1 | 5/2001 |
| WO | WO 01/91744 A1 | 12/2001 |
| WO | WO 02/30355 | 4/2002 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | 2006/019916 | 2/2006 |
| WO | 2006/019916 A1 | 2/2006 |
| WO | WO 2006/019916 | 2/2006 |
| WO | WO 2006/084153 | 8/2006 |
| WO | 2006/102232 A2 | 9/2006 |
| WO | WO 2006/102232 | 9/2006 |
| WO | WO 2007/019165 | 2/2007 |
| WO | WO 2008/005469 | 1/2008 |
| WO | WO 2009/051908 | 4/2009 |
| WO | 2010/054248 A1 | 5/2010 |
| WO | WO 2010/054248 | 5/2010 |
| WO | 2013/020017 A1 | 2/2013 |
| WO | WO 2013/020017 | 2/2013 |
| WO | WO 2013/020215 | 2/2013 |
| WO | WO 2013/130832 | 9/2013 |
| WO | 2014031177 A1 | 2/2014 |

OTHER PUBLICATIONS de Leo, V., et al., "Clomiphene citrate increases insulin-like growth factor binding protein-1 and reduces insulin-like growth factor-I without correcting insulin resistance associated with polycystic ovarian syndrome," Hum. Reprod., vol. 15, pp. 2303-2305 (Nov. 2000).
International Search Report of PCT/US2013/066141 dated Jan. 2, 2014.
Written Opinion of PCT/US2013/066141 dated Jan. 2, 2014.
Chaumeil, J.C., Micronization: A Method of Improving the Bioavailability of Poorly Soluble Drugs, Methods Find. Exp. Clin. Pharmacol., vol. 20, No. 3, pp. 211 (Apr. 1998)—Abstract.
Hill, S., et al., "Enclomiphene, an Estrogen Receptor Antagonist for the Treatment of Testosterone Deficiency in Men," IDrugs: the Investigational Drugs Journal, vol. 12, No. 2, pp. 109-119 (Mar. 2009).
Hobbs, C.J., et al., "Testosterone Administration Increases I nsuli-Like Growth Factor-I Levels in Normal Men," Journal of Clinlical Endocrinology & Metabolism, vol. 77, Issue 3, published online Jan. 14, 2009 (Abstract).
International Preliminary Report on Patentability of PCT/US2009/063621 dated May 19, 2011.
Ito, N., "A Medium-Term Rat Liver Bioassay for Rapid in vivo Detection of Carcinogenic Potential of Chemicals," Cancer Sci., vol. 94, No. 1, pp. 3-8 (Jan. 2003).
Lee, D., et al., PD45-08 "Comparison of Clomiphene Citrate and Transdermal Testosterone Replacement Therapy in Their Influence on Hormonal and Metabolic Changes in the Treatment of Hypogonadism," The Journal of Urology, vol. 193, No. 4S, Supplement, pp. e904-e905 (May 18, 2015).
U.S. Appl. No. 14/380,342—Non-Final office action dated Jul. 25, 2016.
U.S. Appl. No. 14/236,868—Final office action dated Oct. 20, 2016.
U.S. Appl. No. 14/896,043—Non-final office action dated May 13, 2016.
ACCE Clinical Practice Guidelines for the Evaluation and Treatment of Hypogonadism in Adult Male Patients (Nov. 1996).
Adamopoulos, et al., Fertility and Sterility, vol. 80, No. 4, pp. 914-920 (Oct. 2003).
Adashi, Eli, Y., "Clomiphene Citrate: The Case for A Monoisomeric Preparation," Bailliere's Clinical Obstetrics and Bynaecology, vol. 7, No. 2, pp. 331-347 (Jun. 1993).
Agarwal, et al., "Male Sexual Dysfunction After Stroke," J Assoc. Physicians India, vol. 37, No. 8, pp. 505-507 (Aug. 1989).
Anonymous: "Zonagen Presents Data for Androxal in the Treatment of Hypogonadal Men and Data for Progenta as a Potential New Approach in the Treatment of Breast Cancer," News Release, The Healthcare Sales & Marketing Network, XP-002352050, Sep. 2, 2004.
Bandhauer, K., et al., "Varicocele: Spermiogram, Testicular Biopsy, Plasma Testosterone. Results of Therapy," Urologe—Ausgabe A, vol. 16, No. 3, pp. 154-157 (May 1977).
Banner, A., et al., "Emerging Role of Corticosteroids in Chronic Obstructive Pulmonary Disease," The Lancet, vol. 354, pp. 440-441 (Aug. 7, 1999).
Barg, P., et al., "Male Factor: Clinical Evaluation of the Semen Analysis," Infert. Reprod. Med. Clin. North Amer., vol. 2, pp. 333-340 (Apr. 1991).
Bartsch, G., "The Effect of Antiestrogen, Antiandrogen, and the Prolactin Inhibitor 2 Bromo-'alpha!-ergocriptine on the Stromal Tissue of Human Benign Prostatic Hyperplasia. Correlation of Sterological Data and Plasma Hormones," Database Embase; Elsevier Science Publishers, Amsterdam, NL, Jan. 1981, vol. 18, No. 4, pp. 308-312.
Baumann, R. Jeffrey, et al., "Clomiphene Analogs with Activity In Vitro and In Vivo Against Human Breast Cancer Cells," Biochemical Pharmacology, vol. 55, pp. 841-851 (Mar. 1, 1998).
Ben-Jonathan, N., et al., "Dopamine as a Prolactin (PRL) Inhibitor," Endocr. Rev. 22(6), pp. 724-63 (Dec. 2001).
Bitonti, A., J., et al., "Antiproliferative Activity of Enclomiphene and Analogs with Extended Diethylaminoalkoxy Sidechains Against Human Breast Cancer Cells in Vitro and Human Tumor Xenografts in Nude Mice," Proceedings of the Annual Meeting of the American Association for Cancer Research, vol. 35, pp. 267 (Apr. 13, 1994).
Bhasin, S., et al., "Testosterone Therapy in Adult Men with Androgen Deficiency Syndromes: An Endocrine So Society Clinical Practice Guideline," J. Clin Endocrin, Metabol., vol. 91, pp. 1995-2010 (Jun. 2006).
Borghouts, L., et al., "Exercise and Insulin Sensitivity: A Review" Int J Sports Med, vol. 21, No. 1, pp. 1-12 (Jan. 2000) Abstract.
Boyanov, M., et al., "Testosterone Supplementation in Men with Type 2 Diabetes, Visceral Obesity and partial Androgen Deficiency," The Aging Male, vol. 6, pp. 1-7 (Feb. 14, 2003).
Breznik, R., et al., "Effectiveness of Antiestrogens in Infertile Men,"Arch. Androl., vol. 31, No. 1, pp. 43-48 (Jan. 1, 1993).
Brody, J., "Sperm Found Especially Vulnerable to Environment," The New York Times, Mar. 10, 1981.
Broulik, P.D., "Tamoxifen Prevents Bone Loss in Castrated Male Mice," Hormone and Metabolic Research, Thieme-Stratton, Stuttgart, DE, vol. 32, No. 5, pp. 181-184 (Feb. 2000) XP009041862.

(56) References Cited

OTHER PUBLICATIONS

Bryant, H. U., "The Pharmacology of Selective Estrogen Receptor Modulators," Principles of Bone Biology (3rd Edition), vol. 1, Chapter 41, pp. 887-919 (2008) Abstract.

Burghardt, R., et al., "Gap Junction Modulation in Rat Uterus. III. Structure-Activity Relationships of Estrogen Receptor-Binding Ligands on Myometrial and Serosal Cells," Biol. Reprod. vol. 36, No. 3, pp. 741-751 (Apr. 1, 1987).

Casaburi, R., et al., "Effects of Testosterone and Resistance Training in Men with Chronic Obstructive Pulmonary Disease," American Journal of Respiratory and Critical Care Medicine, vol. 170, pp. 870-878 (Jul. 15, 2004).

Chakraborty, P. et al., "Effects of Long-Term Treatment With Estradiol or Clomiphene Citrate on Bone Maintenance, and Pituitary and Uterine Weights in Ovariectomized Rats," J. Steroid Biochem. Molec. Biol., vol. 40, No. 4-6, pp. 725-729 (Dec. 31, 1991).

Chander, S., et al., "The Biological Evaluation of Novel Antioestrogens for the Treatment of Breast Cancer," Critical Reviews in Oncology, vol. 15, No. 3, pp. 243-269 (Dec. 1, 1993).

Chang, Ching-Fong, et al., "Stimulation of Ovulation in Ayu Plecoglossus-altivelis by Treatment with Antiestrogens and Luteinizing Hormone-Releasing Hormone Analog," Aquaculture, vol. 101, Nos. 3-4, pp. 329-336 (Feb. 15, 1992).

Check, J., et al., "Empirical Therapy of the Male with Clomiphene in Couples with Unexplained Infertility" Int. Journal Fertil., vol. 34(2), pp. 120-122 (Dec. 1988).

Clark, James H., et al., "Agonistic and Antagonistic Effects of Clomiphene Citrate and Its Isomers," Biology of Reproduction, vol. 25, pp. 667-672 (1981).

Clomid Information Sheet (available online at http//clomid.us) accessed Mar. 2, 2011.

Cooper, A., et al., "The Effects of Clomiphene in Impotence A Clinical and Endocrine Study," British Journal of Psychiatry, vol. 120, pp. 327-330 (Mar. 1972).

Cunningham, G., et al., "Testosterone Replacement Therapy and Sleep-Related Erections in Hypogonadal Men," J. Clin. Endocrinol. Metab., vol. 70, No. 3, pp. 792-797 (Mar. 1990).

Dangprasit, P., et al., "Development of Diclofenac Sodium Controlled Release Solid Dispersions by Spray Drying Using Optimization Strategy I. Powder Formulation," Drug. Devel. And Industrial Pharm. 21(20), pp. 2323-2337 (Jan. 1, 1995).

Davidson, J., et al., "Effects of Androgen on Sexual Behavior in Hypogonadal Men," J. Clin. Endocrinol. Metab., vol. 48, No. 6, pp. 955-958 (Jun. 1979).

Debigare, R., et al., "Peripheral Muscle Wasting in Chronic Obstructive Pulmonary Disease," American Journal of Respiratory and Critical Care Medicine, vol. 164, pp. 1712-1717 (Nov. 1, 2001).

De Boer, et al., "Letrozole normalizes serum testosterone in severely obese men with hypogonadotropic hypogonadism" Diabetes, Obesity and Metabolism, vol. 7, No. 3, pp. 211-215 (May 1, 2005).

de Leo, V., et al., "Clomiphene Citrate Increases Insulin-Like Growth Factor Binding Protein-1 and Reduces Insulin-Like Growth Factor-I Without Correcting Insulin Resistance Associated with Polycystic Ovarian Syndrome," Human Reproduction, vol. 15, No. 11, pp. 2302-2305 (Nov. 1, 2000).

Drew, A., "Letter: Possible Teratogenic Effect of Clomiphene," Developmental Medicine and Child Neurology, vol. 16, No. 2, pp. 276 (1974).

Dunn, S., et. al., "Insulin-like Growth Factor 1 (IGF-1) Alters Drug Sensitivity of HBL100 Human Breast Cancer Cells by Inhibition of Apoptosis Induced by Diverse Anticancer Drugs," Cancer Research, vol. 57, pp. 2687-2693 (Jul. 1, 1997).

Eastell, R., "Effect on Aromatase Inhibitor on BMD and Bone Turnover Markers: 2-Year Results of the Anastrozole, Tamoxifen, Alone or in Combination (ATAC) Trial (18233230)," Journal of Bone and Mineral Research, vol. 21, No. 8, pp. 1215-1223 (May 22, 2006).

Eil, C., "Ketoconazole Binds To The Human Androgen Receptor," Hormone and Metabolic Research, vol. 24, No. 8, pp. 367-370 (Aug. 1992).

Elanjian, S., "Clomiphene for Male Infertility," Journal of Pharmacy Technology, vol. 12, No. 3, pp. 102-104 (May 1, 1996).

EP Supplementary Search Report of EP 02748104 dated Jun. 24, 2005.

EP Supplementary Search Report of EP 06720243 dated Aug. 6, 2008.

EP Supplementary Search Report of EP 06738985 dated Aug. 15, 2008.

EP Supplementary Search Report of EP 06800648 dated Jul. 21, 2008.

EP Extended Search Report for EP 11153365.9 dated Jan. 20, 2012.

Epstein, J., "Clomiphene Treatment in Oligospermic Infertile Males," Fertility and Sterility, vol. 28, No. 7, pp. 741-745 (Jul. 31, 1977).

Ernst, S., et al., "Stereochemistry of Geometric Isomers of Clomiphene: A Correction of the Literature and A Reexamination of Structure-Activity Relationships," J. Pharmaceut. Sci., vol. 65, No. 1, pp. 148-150 (Jan. 1, 1976).

Excerpt on www.medscape.com from Drug Ther. Perspect., "Toremifene: Antiestorgen for Postmenopausal Breast Cancer," vol. 10, pp. 1-5 (1997).

Feldman, H., et al., "Age Trends in the Level of Serum Testosterone and Other Hormones in Middle-Aged Men: Longitudinal Results from the Massachusetts Male Aging Study," J Clin Endocrinol Metab. 87(2), pp. 589-598 (Feb. 2002).

Anonymous: Ferring Arzneimittel: "Clomifen Ferring 50 mg Tabletten," (http://www.fachinfo.de/data/fi/jsearch?wirkstoff retrieved on May 31, 2011) pp. 1-5 (XP007918978).

Fitzpatrick, S., et al., "Effect of Estrogen Agonists and Antagonists on Induction of Progesterone Receptor in a Rat Hypothalamic Cell Line," Endocrinology, vol. 140, No. 9, pp. 3928-3937 (Sep. 1999).

Fuse, H., et al., "Changes in Seminal Plasma Transferring Concentration Following Administration of Clomiphene Citrate," Archives of Andrology, vol. 31, pp. 139-145 (Jan. 1, 1993).

Ganchev, B., et al., "Quantification of Clomiphene Metabolite Isomers in Human Plasma by Rapid-Resolution Liquid Chromatography-Electrospray Ionization-Tandem Mass Spectrometry," Anal. Bioannal. Chem., vol. 400, pp. 3429-3441 (May 1, 2011).

Garg, A., "Medical progress: Acquired and Inherited Lipodystrophies," New England Journal of Medicine, vol. 35, No. 12, pp. 1231-1232 (Mar. 18, 2004).

Glasier, A., et al., "A Comparison of the Effects on Follicular Development Between Clomiphene Citrate its Two Separate Isomers and Spontaneous Cycles," Human Reproduction, vol. 4, No. 3, pp. 252-256 (Apr. 1989).

Grinenko, G., et al., Khimiko-farmatsevticheskii Zhurnal, vol. 23, No. 1, pp. 118-123 (Jan. 1989).

Guay A., et al., "Results of Double Blinded Treatment With Clomiphene Citrate In Patients With Hypogoadotropic Hypogonadism," Annual Meeting of the Endocrine Society, Abstract No. 386, (Jun. 1993).

Guay, A., et al., "Effect of Raising Endogenous Testosterone Levels in Impotent Men with Secondary Hypogonadism: Double Blind Placebo-Controlled Trial with Clomiphene Citrate," Journal of Clinical Endocrinology and Metabolism, vol. 80, No. 12, pp. 3546-3552 (May 4, 1995).

Guay, A., et al., "Possible Hypothalamic Impotence," Urology, vol. 38, No. 4, pp. 317-322 (Oct. 1991).

Guay, A., et al., "Clomiphene Increases Free Testosterone Levels in Men with Both Secondary Hypogonadism and Erectile Dysfunction: Who Does and Does Not Benefit?" Internatl. J. Ompot. Res., vol. 15, No. 3, pp. 156-165 (Jun. 2003).

Guzick, D., et al., "Sperm Morphology, Motility and Concentration in Fertile and Infertile Men," N. Engl. J. Med., vol. 345, pp. 1388-1393 (Nov. 8, 2001).

Hanus, M., et al., "Antiestrogens (Tamoxifen) in the Alternative Therapy of Benign Prostatic Hyperplasial," US National Library of Medicine, Bethesda, MD, Database Medline, vol. 72, No. 7, pp. 316-318 (Oct. 1993).

(56) References Cited

OTHER PUBLICATIONS

Haskell, S., "Selective Estrogen Receptor Modulators," Southern Medical Journal, vol. 96, No. 5, pp. 469-476 (May 2003).
Hayashi, Norio, et al., Hinyokika Kiyo (Acta Urologica Japonica), vol. 34, No. 5, pp. 847-50 (1988) with English translation.
Healthline, Hypogonadotropic Hypogonadism, reviewed by Robert Cooper, MD, accessed Oct. 15, 2010 pp. 1-2.
Heidegger, et al., "Targeting the Insulin Like Growth Factor Network in Cancer Therapy," Cancer Biology & Therapy, vol. 11, No, 8, pp. 701-707 (Apr. 2011).
Herzog, A. G., "Reproductive Endocrine Considerations and Hormonal Therapy for Men with Epilepsy," Epilepsia, Raven Press Ltd., New York, US, vol. 32, No. Suppl. 6, pp. S34-S37, (Dec. 1, 1991).
Hirshkowitz, M., et al., "Androgen and Sleep-Related Erections," J. Psychosomatic Research, vol. 42, No. 6, pp. 541-546 (Jun. 30, 1997).
Homonnai, Z., et al., "Clomiphene Citrate Treatment in Oligozoospermia: Comparison Between Two Regimens of Low-Dose Treatment," Fertility and Sterility., vol. 60, No. 5, pp. 801-804 (Nov. 30, 1988).
International Preliminary Examination Report of PCT/US2002/21524 dated Mar. 3, 2006.
International Preliminary Report on Patentability of PCT/US2005/02500 dated Jan. 16, 2007.
International Preliminary Report on Patentability of PCT/US2006/003882 dated Aug. 7, 2007.
International Preliminary Report on Patentability of PCT/US2006/030053 dated Feb. 5, 2008.
International Preliminary Report on Patentability of PCT/US2006/10022 dated Sep. 25, 2007.
International Preliminary Report on Patentability of PCTUS2013/066141 dated May 5, 2015.
International Preliminary Report on Patentability of PCT/US2014/040704 dated Dec. 8, 2015.
International Search Report and Written Opinion of PCT/US2015/67036 dated Mar. 11, 2016.
International Search Report and Written Opinion of PCT/US2014/040704 dated Oct. 15, 2014.
International Search Report and Written Opinion of PCT/US2013/028356 dated Apr. 16, 2013.
International Search Report of PCT/US2013/032659 dated Jul. 19, 2013.
International Search Report and Written Opinion of PCTUS2013/026178 dated Jul. 22, 2013.
International Search Report of PCT/US2002/21524 dated Jun. 18, 2003.
International Search Report of PCT/US2005/02500 dated Nov. 24, 2005.
International Search Report of PCT/US2006/003882 dated Aug. 14, 2006.
International Search Report of PCT/US2006/10022 dated Jan. 10, 2007.
International Search Report of PCT/US2006/30053 dated Dec. 22, 2006.
International Search Report of PCT/US2008/075433 dated Dec. 19, 2008.
International Search Report of PCT/US2009/063621 dated Dec. 28, 2009.
International Search Report and Written Opinion of PCT/US2012/049451 dated Oct. 11, 2012.
International Search Report and Written Opinion of PCT/US2015/019493 dated Jun. 3, 2015.
International Search Report and Written Opinion of PCT/US2015/63248 dated Feb. 8, 2016.
Jarow, J., "Nonsurgical Treatment of Male Infertility: Empiric Therapy," Therapy, Chapter 23, pp. 410-422 (1991).
Jiann, B., et al., "Effect of Clomiphene on $Ca^{2+}$ Movement in Human Prostate Cancer Cells," Life Sciences, vol. 70, No. 26, pp. 3167-3178 (May 2002).
Jimenez, M., et al., "Clomiphene Prevents Cancellous Bone Loss from Tibia of Ovariectomized Rats," vol. 138, No. 5, pp. 1794-1800 (May 1, 1997).
Johansen, L. M., et al., "FDA-Approved Selective Estrogen Receptor Modulators Inhibit Ebola Virus Infection," Sci. Tansl. Med., vol. 5, pp. 190ra79-190ra79 (Jun. 19, 2013).
Jones, T. Hugh., "Testosterone Associations with Erectile Dysfunction, Diabetes, and the Metabolic Syndrome," European Urology Supplements, vol. 6, pp. 847-857 (Oct. 31, 2007).
Kaaks, R., "Nutrition, Insulin, IGF-1 Metabolism and Cancer Risk: A Summary of Epidemiological Evidence," Biology of IGF-1; Its Interaction with insulin in Health and Malignant States, vol. 262, Wiley, Chichester Novartis Foundation Symposium 262), pp. 247-260 (Jun. 10, 2005).
Kadioglu, et al., Treatment of Idiopathic and Postvaricocelectomy Oligozoospermia with Oral Tamoxifen Citrate, BJU Int., vol. 83, No. 6, pp. 646-648 (Apr. 1, 1999).
Karrer, P., "Monovalent Hydroxyl Function," Organic Chemistry, 3rd Edition, Elsevier Publishing Co., pp. 94-105 (1947).
Ke, H. Zhu, et al., "Lasofoxifene (CP-336,156), A Selective Estrogen Receptor Modulator, Prevents Bone Loss Induced by Aging and Orchidectomy in the Adult Rat," Endocrinology, vol. 141, No. 4, pp. 1338-1344 (2000) XP001170303.
Kharenko, A., et al., "Controlled Release From Oral Formulations Based on Interpolymeric Polymethacrylic Acid—Polyethylene Glycol Complex," Proceed. Intern. Symp. Control Rel. Bioact. Mater., vol. 22, pp. 232-233 (1995).
Kidd, S., et al., "Effects of male age on semen quality and fertility: A review of the literature," Fertility and Sterility, vol. 75, pp. 237-248 (Feb. 28, 2001).
Kotoulas, I., et al., "Tamoxifen Treatment in Male Infertility. I. Effect on spermatozoa," Fertil. Steril., vol. 61, No. 5, pp. 911-914 (May 31, 1994).
Laghi, F., et al., "Respiratory and Skeletal Muscles in Hypogonadal Men with Chronic Obstructive Pulmonary Disease," American Journal of Respiratory and Critical Care Medicine, vol. 171, pp. 598-605 (Mar. 15, 2005).
Lewis, B., et al., "Medical Implication of the Biological Clock," JAMA, vol. 296, pp. 2369-2371 (Nov. 15, 2006).
Lim, V., et al., "Restoration of Plasma Testosterone Levels in Uremic Men with Clomiphene Citrate," Journal of Clinical Endocrinology and Metabolism, New York, US vol. 43, No. 6, pp. 1370-1377 (Dec. 1976) XP 009041861.
Lonning, P., "Comparing cost/utility of giving an aromatase inhibitor as monotherapy for 5 years versus sequential administration following 2-3 or 5 years of tamoxifen as adjuvant treatment for postmenopausal breast cancer," Annals of Oncology, vol. 17, pp. 217-225 (Feb. 2006).
Lund, et al., "Testosterone and Andropause: The Feasibility of Testosterone Replacement Therapy in Elderly Men," Pharmacotherapy, vol. 19, No. 8, pp. 951-956 (Aug. 1, 1999).
Macrochem Press Release (Opeterone Topical Testosterone Cream, (May 12, 2010) accessed online Sep. 20, 2010.
Macleod, J., et al., "The Male Factor in Fertility and Infertility II Spermatozoon Counts in 1000 Men of Known Fertility and in 1000 Cases of Infertile Marriage," J. Urology, vol. 66, pp. 436-449 (Sep. 1951).
Makhsida, N., et al., "Hypogonadism and Metabolic Syndrome: Implications for Testosterone Therapy," J. Urology, vol. 174, pp. 827-834 (Sep. 30, 2005).
Matsumoto, A., et al., "Human Chorionic Gonadotropin and Testicular Function: Stimulation of Testosterone, Testosterone Precursors, and Sperm Production Despite High Estradiol Levels," Journal of Clinical Endocrinol. And Metab., vol. 56, No. 4, pp. 720-728 (Apr. 1983).
McKinlay, J., et al., "The Questionable Physiologic and Epidemiologic Basis for a Male Climacteric Syndrome: Preliminary Results from the Massachusetts Male Aging Study," Maturitas, vol. 11, No. 2, pp. 103-115 (Jun. 30, 1989).
Mazzarino, M., et al., "A Mass Spectrometric Approach for the Study of the Metabolism of Clomiphene, Tamoxifen and

(56) References Cited

OTHER PUBLICATIONS

Toremifene by Liquid Chromatography Time-of-flight Spectroscopy," European Journal of Mass Spectrometry, vol. 14, No. 3, pp. 171-180 (Aug. 1, 2008).
Medical Information of Henan Province, "Report on 42 Cases of Treating Male Sterility with Clomiphene," vol. 2, No. 2 (Feb. 2001) (Translation).
Merck Index, 13th Ed., Entry 2410, p. 417 (2001).
Meshali, M., et al., "Effect of Interpolymer Complex Formation of Chitosan With Pectin or Acaxia on the Release Behaviour of Chlorpromazine HC1" Int. J. Phar., vol. 89, pp. 177-181 (Feb. 5, 1993).
Meso-RX, Clomid & Arimidex for Secondary Hypogonadism, Discussion in Men's Health Forum started by rbauer (Apr. 18, 2007).
Mikkelson, T., et al., "Single-Dose Pharmacokinetics of Clomiphene Citrate in Normal Volunteers," Fertility and Sterility, vol. 46, No. 3, pp. 392-396 (Sep. 30, 1986).
Morales, A., et al., "Andropause: A Misnomer For A True Clinical Entity," J. Urol., vol. 163, No. 3, pp. 705-712 (Mar. 31, 2000) Abstract.
National Institute of Diabetes and Digestive and Kidney Diseases (NIDDK) website (accessed online at http://diabetes.niddk.nih.gov on Oct. 14, 2014).
Nicholson, T., et al., MP48095, Combination Therapy with an Aromatase Inhibitor is Needed in One Out of Six Hypogonadal Men Treated with Clomiphene Citrate, The Journal of Urology, vol. 191, No. 4S, Supplement (May 19, 2014) Abstract.
Parini, P., et al., "Importance of Estrogen Receptors in Hepatic LDL Receptor Regulation," Ateriosclerosis, Thrombosis, and Vascular Biology, vol. 17, pp. 1800-1805 (Sep. 1, 1997).
PCT Written Opinion of PCT/US02/21524 dated Nov. 25, 2005.
PCT Written Opinion of PCT/US05/02500 dated Sep. 14, 2006.
PCT Written Opinion of PCT/US06/003882 dated Aug. 4, 2007.
PCT Written Opinion of PCT/US06/10022 dated Jan. 10, 2007.
PCT Written Opinion of PCT/US06/30053 dated Dec. 22, 2006.
PCT Written Opinion of PCT/US08/075433 dated Dec. 19, 2008.
PCT Written Opinion of PCT/US09/063621 dated Dec. 28, 2009.
Petak, S., et al., American Association of Clinical Endocrinologists Medical Guidelines for Clinical Practice for the Evaluation and Treatment of Hypogonadism in Adult Male Patients, Endocrine Practice, vol. 8, pp. 440-456 (Nov./Dec. 2002).
Purvis, K., et al., "Stability of Sperm Characteristics in Men with Disturbances in Sperm Quality," Int. Journal Androl., 12, pp. 171-178 (Jun. 1989).
Rao, et al., Synthesis of Carbon-14 Labeled Clomiphene. Journal of Labelled Compounds and Radiopharmaceuticals, vol. 22, No. 3, pp. 245-255 (Mar. 1, 1985) Abstract.
Ronnberg, L., "The Effect of Clomiphene Treatment on Different Sperm Parameters in Men with Idiopathic Oligozoospermia," Andrologia, vol. 12, No. 3, pp. 261-265 (Dec. 1979).
Ross., J.W., et al., "Effect of Clomiphene Citrate and Its Isomers on Sexual Behavior in Ovariectomized Rats," Endocrinology, vol. 92, No. 4, pp. 1079-1083 (Apr. 1973) (Abstract).
Ruenitz, P., C., "Rabbit Liver Microsomal Metabolism of Enclomiphene," Drug Metabolism and Disposition, vol. 9, No. 5, pp. 456-460 (Sep. 1, 1981).
Ruenitz, et al., Cancer Research, vol. 47, pp. 4015-4109 (Aug. 1, 1987).
Ruenitz, Peter, et al., "Phenolic Metabolites of Clomiphene: [(E,Z)-2-[4-(1,2-Diphenyl-2-chlorovinyl)phenoxy]ethyl]diethylamine. Preparation, Electrophilicity, and Effects in MCF 7 Breast Cancer Cells," J. Med. Chem., vol. 32, pp. 192-197 (Jan. 1989).
Sankaran M.S., et al., "Effects of Progesterone, Oestradiol and/or Clomiphene on Liver Glycogen and Blood Glucose in Intact and Adrenalectomised Rats During Delayed Implantation," acta Endocrinologica, vol. 76, pp. 678-688 (Aug. 1, 1974).
Schultheiss, D., et al., "Testosterone Therapy in the Ageing Male: What About the Prostate?" Andrologia, vol. 36, No. 6, pp. 357-365 (May 4, 2004).

Schweikert, H., et al., "Effects of Estrogen Deprivation on Human Benign Prostatic Hyperplasia," Steroid Biochem Mol Biol., vol. 44, No. 4-6, pp. 573-576 (Mar. 31, 1993).
Shanis, B., et al., Adverse Effect of Clomiphene Citrate on Sperm Morphology, Arch. Androl., vol. 21, pp. 109 (Jan. 1, 1991).
Shida, K., et al., "Medical Treatment of Neoplasm with Steroids and Antisteroids," Chemical Abstracts Service, XP-002352053, May 12, 1984.
Shirai, Takashi, et al., Saishin-Igaku (Latest Medical Science), vol. 45, No. 11, pp. 2250-2254 (1990) with English translation.
Singh, S., et al., "Changes in Fructose & Citric Acid in Accessory Glands of Reproduction of Rats Following Long-Term Treatment With Isomers of Clomiphene Citrate," Indian Journal of Experimental Biology, vol. 11, pp. 23-26 (Jan. 1973).
Soderguard, R., et al., "Calculation of Free and Bound Fractions of Testosterone and Estradiol-17β to Human Plasma Proteins at Body Temperature," J. Steroid Biochem, vol. 16, pp. 801-810 (Jun. 1982).
Sokol, R., et al., "A Controlled Comparison of the Efficacy of Clomiphene Citrate in Male Infertility," No. 5, Fertil and Steril, vol. 49, pp. 865-870 (May 31, 1988).
Spitz, I., "Progesterone Receptor Antagonists," Current Opinion, vol. 7, No. 10, pp. 882-890 (2006).
Stahl, F., et al., "Effects of Tamoxifen on the Levels of luteinizing Hormone (LH), Follicle Stimulating Hormone FSH), Prolactin (PRL), 17 beta-oestradiol (E2), and free dihydrotestosterone (DHT) in blood of patients with Benign Prostatic Hyperplasia," US National Library of Medicine, Bethesda, MD, US, vol. 82, No. 1, pp. 21-28 (Jul. 1983).
Stedman's Medical Dictionary, William and Wilking, pp. 1312, 1439 & 1798-1799 (1995).
Steiner, M., S., et al., "Antiestrogens and Selective Estrogen Receptor Modulators Reduce Prostte Cancer Risk," World J Urol., vol. 21, pp. 31-36 (Feb. 14, 2003).
Sternbach, et al., "Age-associated Testosterone Decline in Men: Clinical Issues for Psychiatry," Am. J. Psychiatry, vol. 155, No. 10, pp. 1310-1318 (1998) Abstract.
Sterochemistry of Geometric Isomers of Clomiphene: A Correction of the Literature and A Reexamination of Structure-Activity Relationships, Journal of Pharmaceutical Science, vol. 65, No., pp. 184-150 (176) XP009056304.
Suzuki, et al., "Endocrine Environment of Benign Prostatic Hyperplasia: Prostate Size and Volume are Correlated with Serum Estrogen Concentration," Scand. J. Urol. Nephrol., vol. 29, No. 1, pp. 65-8 (1995) Abstract.
Takihara, Hiroshi, Jin to Toseki (Kidney and Dialysis) vol. 41, Special Edition, pp. 759-761 (1996) with English translation.
Tan, R.S., et al., "An Unusual Case of Vascular Hypogonadism Treated with Clomiphene Citrate and Testosterone Replacement," Andrologia, vol. 41, No. 1, pp. 63-65 (Feb. 1, 2009).
Teodosio Da Ros, C., et al., "Twenty-Five Milligrams of Clomiphene Citrate Presents Positive Effect on Treatment of Male Testosterone Deficiency—a Prospective Study," Int. Braz J. Urol., vol. 38, No. 4, pp. 512-518 (Jul.-Aug. 2012).
Tenover, J., et al., "Effects of testosterone supplementation in the aging male." J Clin. Endocrine. Metabol., vol. 75, No. 4, pp. 1092-1098 (Oct. 1992).
Tenover, J., et al., "Male Hormone Replacement Therapy Including Andropause," Endrocrinology and Metabolism Clinics of North America, W.B. Saunders Company, Philadelphia, US, Dec. 1998, vol. 27, No. 4, pp. 969-987 XP008019800.
Tenover, J., et al., "Serum Bioactive and Immunoreactive Follicle-Stimulating Hormone Levels and the Response to Clomiphene in Healthy Young and Elderly Men," Journal Clinical Endocrinol. And Metab., vol. 64, No. 6, pp. 1103-1108 (Jun. 1987).
Tenover, J., et al., "The Effects of Aging in Normal Men on Bioavailable Testosterone and Luteinizing Hormone Secretion: Response to Clomiphene Citrate," Journal Clinical Endocrinol. Metab. , vol. 65, No. 6, pp. 1118-1126 (Dec. 1987).
Turner, R., et al., "Differential Responses of Estrogen Target Tissues in Rats Including Bone to Clomiphene, Enclomiphene, and Zuclomiphene," vol. 139, No. 9, pp. 3712-3720 (Sep. 1, 1998).
U.S. Pharmacopeia, United States Phamacopeia, 26$^{th}$ Ed., pp. 484-485 (2003).

(56) References Cited

OTHER PUBLICATIONS

Vippagunta, et al., "Crystalline solids" Advanced Drug Delivery Reviews, vol. 48, No. 1, pp. 3-26 (May 16, 2001).
Virginia Mason Medical Center (available online at www.virginiamason.org) accessed Mar. 2, 2011, "What are Normal Blood Glucose Levels?".
Wang, C., et al., "Comparison of the Effectiveness of Placebo, Clomiphene Citrate, Mesterolone, Pentoxifylline, and Testosterone Rebound Therapy for the Treatment of Idiopathic Oligospermia," Fertility and Sterility, vol. 40, No. 3, pp. 358-365 (Sep. 30, 1983).
Weissenberg, R., et al., "The Effect of Clomiphene Citrate and is Zu or En isomers on the Reproductive System of the Immature Male Rate," Andrologia, vol. 24, pp. 161-165 (1992).
Wiehle, R.D., et al., "Androxal™ (oral enclomiphene citrate) Raises Free and Total Serum Testosterone in Hypogonadal Men: Comparison with Androgel 1%®," Fertility and Sterility, vol. 82, pp. 2004-2009, (Oct. 19, 2004).
Williams, D., et al., Foye's Priciples of Medicinal Chemistry 5 Edition, Part I/Principles of Drug Discovery, Lippincott Williams & Wilkins, p. 50 (2002).
Written Opinion of Singapore Patent Applc. 2007-05640-1 dated Jul. 9, 2008.
Young, R., et al., "A Short-Term Comparison of the Effects of Clomiphene Citrate and Conjugated Equine Estrogen in Menopausal/Castrate Women," Int. J. Fertil., vol. 36, No. 3, pp. 167-171 (1991).
Young, R., et al., "Qualitative Differences in Estrogenic/Antiestrogenic Effects of Clomiphene and Zuclomiphene," Int. J. Fertil., vol. 36, No. 5, pp. 291-295 (Dec. 1990).
Young S., "Serum Concentrations of Enclomiphene and Zuclomiphene Across Consecutive Cycles of Clomiphene Citrate Therapy in Anovulatory Infertile Women," Fertility and Sterility, vol. 71, No. 4, pp. 639-644 (Apr. 30, 1999).
U.S. Appl. No. 12/205,456 Restriction Requirement dated Apr. 30, 2010.
U.S. Appl. No. 12/205,456 Non-Final Office Action dated Sep. 28, 2010.
U.S. Appl. No. 12/205,456 Final Office Action dated Mar. 7, 2011.
U.S. Appl. No. 12/205,456 Non-Final Office Action dated Apr. 24, 2012.
U.S. Appl. No. 12/205,456 Notice of Allowance dated Oct. 15, 2012.
U.S. Appl. No. 12/838,036—Notice of Allowance dated Sep. 3, 2013.
U.S. Appl. No. 12/838,036 Non-Final Office Action dated Oct. 21, 2010.
U.S. Appl. No. 12/838,036 Final Office dated May 16, 2011.
U.S. Appl. No. 13/590,045 Non-Final Office Action dated Oct. 9, 2012.
U.S. Appl. No. 13/590,045 Response to Amendment under Rule 312 dated Jun. 11, 2013.
U.S. Appl. No. 13/590,045—Notice of Allowance dated Apr. 30, 2013.
U.S. Appl. No. 10/427,768 Examiner's Interview Summary Record dated Nov. 19, 2007.
U.S. Appl. No. 10/427,768 Final office action dated Apr. 6, 2006.
U.S. Appl. No. 10/427,768 Non-final office action dated May 29, 2007.
U.S. Appl. No. 10/427,768 Non-final office action dated Oct. 12, 2005.
U.S. Appl. No. 10/427,768 Notice of Allowance and Examiner's Amendment dated Dec. 27, 2007.
U.S. Appl. No. 10/427,768 Restriction Requirement dated May 23, 2005.
U.S. Appl. No. 10/483,458 Notice of Allowance dated Apr. 21, 2010.
U.S. Appl. No. 10/483,458 Final Office dated Mar. 17, 2010.
U.S. Appl. No. 10/483,458 Non-final office action dated Jul. 20, 2009.
U.S. Appl. No. 10/483,458 Advisory Action dated Jan. 16, 2009.
U.S. Appl. No. 10/483,458 Final office action dated Nov. 19, 2008.
U.S. Appl. No. 10/483,458 Non-final office action dated Feb. 13, 2008.
U.S. Appl. No. 10/483,458 Restriction Requirement dated Oct. 25, 2007.
U.S. Appl. No. 10/712,546 Non-final office action dated Mar. 15, 2006.
U.S. Appl. No. 10/712,546 Notice of Allowance dated Sep. 29, 2006.
U.S. Appl. No. 10/712,546 Restriction Requirement dated Nov. 10, 2005.
U.S. Appl. No. 11/750,190 Restriction Requirement dated Mar. 27, 2009.
U.S. Appl. No. 11/750,190 Non-final office action dated Aug. 11, 2009.
U.S. Appl. No. 11/750,190 Notice of Allowance dated Jan. 8, 2010.
U.S. Appl. No. 11/750,190 Notice of Allowance dated Feb. 5, 2010.
U.S. Appl. No. 11/571,150 Restriction Requirement dated Aug. 31, 2009.
U.S. Appl. No. 11/571,150 Non-final office action dated Oct. 14, 2009.
U.S. Appl. No. 11/997,858 Restriction Requirement dated Aug. 28, 2009.
U.S. Appl. No. 11/815,542 Restriction Requirement dated Aug. 31, 2009.
U.S. Appl. No. 11/815,542 Non-final office action dated Oct. 15, 2009.
U.S. Appl. No. 11/815,542 Final Office action dated Mar. 30, 2010.
U.S. Appl. No. 11/815,542 Advisory Action dated Jun. 16, 2010.
U.S. Appl. No. 11/815,542 Non-final office action dated May 10, 2011.
U.S. Appl. No. 11/815,542 Final Office action dated Nov. 15, 2011.
U.S. Appl. No. 11/815,542 Non-Final Office Action dated Feb. 28, 2012.
U.S. Appl. No. 11/815,542 Notice of Allowance dated Apr. 18, 2012.
U.S. Appl. No. 11/814,068 Non-final office action dated Apr. 12, 2011.
U.S. Appl. No. 13/196,688 Notice of Allowance dated Oct. 16, 2012.
U.S. Appl. No. 13/590,045 Notice of Allowance dated Apr. 30, 2013.
U.S. Appl. No. 14/378,573—Non-final office action dated Jan. 22, 2015.
U.S. Appl. No. 14/378,573—Notice of Allowance dated Jun. 10, 2015.
U.S. Appl. No. 14/886,874—Restriction Requirement Feb. 9, 2016.
U.S. Appl. No. 13/764,574—Non-final office action dated Oct. 23, 2014.
U.S. Appl. No. 13/764,574—Restriction Requirement dated Jun. 6, 2014.
U.S. Appl. No. 13/764,574—Final Office action dated Jun. 26, 2015.
U.S. Appl. No. 13/764,574—Non-final office action dated Dec. 17, 2015.
U.S. Appl. No. 13/764,574—Final Office Action dated Jun. 9, 2016.
U.S. Appl. No. 14/380,342—Non-final office action dated Jun. 1, 2015.
U.S. Appl. No. 14/380,342—Final office action dated Dec. 7, 2015.
U.S. Appl. No. 14/085,494—Non-final office action dated Dec. 15, 2014.
U.S. Appl. No. 14/085,494—Final Office Action dated Apr. 19, 2016.
U.S. Appl. No. 14/236,868—Restriction Requirement dated Oct. 2, 2015.
U.S. Appl. No. 14/236,868—Non-final office action dated Feb. 12, 2016.
U.S. Appl. No. 14/421,119—Restriction Requirement dated Oct. 5, 2015.
U.S. Appl. No. 14/421,119—Non-final office action dated May 6, 2016.
U.S. Appl. No. 14/896,043—Non-final office action dated Apr. 22, 2016.

(56) References Cited

OTHER PUBLICATIONS

U.S. Control No. 90/008,024 Non-final office action dated Nov. 1, 2006.
U.S. Control No. 90/008,024 Examiner Interview Summary Record dated Dec. 13, 2006.
U.S. Control No. 90/008,024 Non-final office action dated Jan. 29, 2007.
U.S. Control No. 90/008,024 Final office action dated Jun. 22, 2007.
U.S. Control No. 90/008,024 Examiner Interview Summary Record dated Jul. 25, 2007.
U.S. Control No. 90/008,024 Final office action dated Nov. 16, 2007.
U.S. Control No. 90/008,024 Advisory Action dated Feb. 1, 2008.
U.S. Control No. 90/008,024 Advisory Action dated Mar. 5, 2008.
U.S. Control No. 90/008,024 Examiner's Answer dated Jun. 12, 2008.
U.S. Control No. 90/008,024 Decision on Appeal dated Aug. 28, 2009.
U.S. Control No. 90/008,024 Decision on Request for Rehearing dated Aug. 2, 2010.
U.S. Control No. 90/006,921 Non-final office action dated Sep. 9, 2004.
U.S. Control No. 90/006,921 Examiner's Interview Summary dated Nov. 20, 2004.
U.S. Control No. 90/006,921 Final office action dated Feb. 23, 2005.

* cited by examiner

*p=0.006 **p=0.006

TRANS-CLOMIPHENE FOR USE IN CANCER THERAPY

CROSS-REFERENCE TO RELATED APPLICATIONS

The application claims the benefit of U.S. Provisional Application No. 61/722,013, filed Nov. 2, 2012, the contents of which are incorporated herein by reference.

FIELD OF THE INVENTION

The present invention relates to compositions and methods for treating cancer and associated diseases. Specifically, the present invention relates to the use of a selective estrogen receptor modulator such as trans-clomiphene or a metabolite thereof to treat cancer in a subject by reducing the level of insulin-like growth factor-1 (IGF-1) in the subject.

BACKGROUND

The insulin-like growth factor (IGF) axis involves complex interactions among a number of different signaling factors (IGF-1, IGF-2 and IGF-3), their various cognate binding proteins (IGF-BPs), as well as both IGF, insulin, and IGF-insulin hybrid receptor proteins (IGF-R, INS-R, and IGN-R, respectively). IGFs are growth stimulatory peptides, structurally similar to insulin, that participate in the regulation of mitogenesis, cellular differentiation, and apoptosis. Normally, IGF-1 is produced predominately by the liver and largely functions as an endocrine hormone. Alterations in the IGF-1 signaling pathways have been described in multiple tumors including osteosarcomas, breast, bladder, gynecological, gastrointestinal, prostate and lung cancers. Animal and human studies have shown that in such cancers IGF-1 also functions as a paracrine and autocrine hormone, being produced by the tumor cells and interacting with IGF-R, which is frequently overexpressed by the tumor cells as well. [Arnaldez and Helman, Hematol. Oncol. Clin. North Am., 26:527 (2012)]. Numerous studies have established a relationship between high serum levels of IGF-1 and increased cancer incidence and mortality. Thus, the IGF axis provides new opportunities to develop effective cancer therapeutics. Several therapeutic approaches to exploiting the IGF axis have been explored, including various strategies for blocking IGF-R function as well as increasing the availability of IGF-BPs. [Heidegger, et al., Cancer Biology and Therapy 11:701 (2011)].

IGF-R was first identified as a promising therapeutic target over 20 years ago when Arteaga and Osbourn reported that antibodies against IGF-R inhibited growth of breast cancer cells in vitro [Arteaga and Osborne, Cancer Res 49:6237 (1989)]. Since then, as many as 30 different agents targeting IGF-R have been developed and over 60 clinical trials evaluating anti-IGF-R therapies have been reported [reviewed in Heidegger et al., Cancer Biology and Therapy 11:701 (2011)]. The majority of agents targeting IGF-R are monoclonal antibodies (mAbs), which exhibited good safety profiles in early, Phase I and II testing. However, more recent Phase III trials, in combination with different drug treatments indicated that there may be some problems with this approach. In March 2010, Phase III trials of one of the more successful anti-IGF-R mAbs, figitumumab, used in combination with either paclitaxel or erlotinib (an epidermal growth factor receptor tyrosine kinase inhibitor (EGFR-TKI)) were halted because early results indicated that the combination of drugs was not significantly effective over either drug alone, as well as safety concerns that the combination drug cohort experienced an elevated level of adverse effects. Interestingly, high levels of free IGF-1 appeared to be a marker for resistance to figitumumab therapy [Gualberto et al (2010b) Br J Cancer 104: 68 (2010)]. Significantly, one of the side effects seen in the figitumumab treated group was hyperglycemia, suggesting that that inhibition of IGF-R effects cross-talk with INS-R. Despite this setback, figitumumab and related anti-IGF-R mAbs remain among the best therapeutic candidates available and methods to increase treatment efficacy and prevent or reduce side effects would be invaluable for deploying this drug class in routine clinical use.

One alternative to anti-IGF-R mAb therapy targets the signal transduction tyrosine kinase activity of IGF-R (IGFR-TKI). The biochemical strategy is similar to EGFR-TKI drugs such as gefitinib, erlotinib and others, which have already been approved for treatment of lung, hepatocellular and renal cancers. Essentially, IGFR-TKIs compete for the ATP binding site of IGF-R and block the transition of the receptor to the phosphorylated active conformation. Initial clinical results report similar side effects as observed with IGF-R mAbs, especially with respect to hyperglycemia. Thus, IGFR-TKI treatment seems to suffer the same problems with cross-talk between the IGF-R and INS-R systems. In fact, the effect may be due to more than just cross-talk since the ATP binding domains of IGF-R, INS-R and IGN-R are virtually identical and IGFR-TKI drugs likely bind each of the receptor species with equivalent or nearly equivalent affinity.

A third approach to targeting IGF-R for cancer therapy involves antisense oligonucleotides (IGFR-ASO) that selectively target and destroy IGF-R transcripts prior to translation. Preclinical studies have developed a number of promising candidates, including at least one IGFR-ASO capable of suppressing growth of a paclitaxel resistant prostate tumor model. The specificity of the IGFR-ASO strategy holds great promise for avoiding the cross talk issues observed with IGF-R mAb and IGFR-TKI therapies, in particular the tendency to provoke hyperglycemia. However, the biology of the system is complex and it isn't certain that IGFR-ASOs will prove clinically useful. A pilot clinical study indicated that the IGFR-ASO was well tolerated but this approach suffers from poor half-life and delivery problems. No oral delivery route is available and routine clinical use of such compounds will require overcoming this limitation.

One other aspect of the IGF axis has been explored for its potential as a cancer therapeutic. In this approach, the availability of IGF-BPs is increased to reduce available free IGF capable of activating IGF-R. IGF-BPs are quite selective for their specific cognate IGF and preclinical work has shown that these proteins exhibit pro-apoptotic, anti-proliferative and anti-angiogenic properties. Unfortunately, there are no clinical studies of this approach and not all in vitro results have been replicated in animal models. Though promising, much work remains to be done to develop this strategy into a useful therapy.

Other than the early stage work with IGF-BPs, no method for directly limiting the availability of IGF-1 to limit activation of IGF-R is known. A strategy for reducing the level of IGF-1 available to activate IGF-R, without provoking cross talk between IGF-R and INS-R involving a safe, orally delivered drug would be of great value to the field.

Tamoxifen is a triphenylalkylene derivative that binds to the estrogen receptor (ER). It has both estrogenic and antiestrogenic actions, depending on the target tissue. It is strongly antiestrogenic to mammary epithelial cells, hence its use in both the prevention and treatment of breast cancer. Tamoxifen was originally screened in a program oriented to discovering new contraceptive agents. Although it was not a useful drug for control of fertility, tamoxifen was eventually discovered to be useful for clinical treatment of breast cancer. The therapeutic mechanisms of tamoxifen are complex, the primary effect of tamoxifen is exerted via estrogen receptors, but the drug may also modulate IGF-1 levels as well. However, at least one study reported no change to circulating IGF-1 levels after tamoxifen treatment [Campbell, et al., J. Clin. Pathol: Mol Pathol. 54:307 (2001)]. In vitro studies suggest that tamoxifen may also disrupt IGF-1 autocrine loops in at least some cancer cell types, but has no effect in others [Howe, et al., Cancer Res. 56:4049 (1960].

Tamoxifen is a pro-drug requiring metabolic activation by hepatic cytochrome P450 enzymes. In particular, CYP2D6 is instrumental in converting the pharmaceutically inactive tamoxifen and its most predominate metabolite, N-desmethyltamoxifen to endoxifen (4-hydroxy-N-desmethyl-tamoxifen), the pharmaceutically active form of the drug, which has much higher affinity to the ER than either of its precursors. CYP3A4 also plays a key role in activating tamoxifen or 4-hydroxy-tamoxifen to the N-desmethyl form. Extensive pharmacogenomic analyses of tamoxifen metabolism show that certain human alleles of CYP2D6 are incapable of activating tamoxifen to endoxifen and thus patients with these alleles receive no benefit from treatment with tamoxifen.

Another structurally similar triphenylalkylene derivative with both estrogenic and antiestrogenic activities is clomiphene. Clomiphene blocks normal estrogen feedback on the hypothalamus and subsequent negative feedback on the pituitary. This leads to increases in luteinizing hormone and follicle stimulating hormone. In men, increased levels of these gonadotropins results in the production of higher testosterone levels from the Leydig cells of the testes. In women, these increased levels of gonadotropins results in ovulation. Clomiphene citrate has been used to treat female infertility for many years with a relatively low level of serious side effects.

Ernst et al., J. Pharmaceut. Sci. 65:148 (1976), have shown that clomiphene is a mixture of two geometric isomers which are referred to as cis,-Z-, clomiphene (cis-clomiphene, or zuclomiphene) and trans-,E-, clomiphene, (trans-clomiphene or enclomiphene). Ernst et al. also noted that (the trans-isomer) is antiestrogenic, while the cis-isomer is the more potent and more estrogenic form, but has also been reported to have anti-estrogenic activity [Ibid.]. Recently, the isolated trans-isomer of clomiphene has been developed to treat, inter alia, secondary hypogonadism in men and is currently in Phase III trials as Androxal®.

Like tamoxifen, clomiphene is metabolized to the 4-hydroxy and N-dealkyl forms by the liver enzymes CYP2D6 and CYP3A4, respectively [Ghobadi, et al., Drug Metab. Pharmacokinet 23:101 (2008) and Murdter et al., Hum. Mol. Genet. 21:1145 (2012)]. Murdter has also shown that 4-hydroxy-trans-clomiphene ((E)-4OH-clomiphene) and N-desethyl-4-hydroxy-trans-clomiphene ((E)-DE-4-OH-clomiphene) are strong ligands for the human estrogen receptor [Ibid.]. The fact that both tamoxifen and clomiphene are both activated by the same liver enzymes suggests that other triphenylalkylene derivatives may also produce active pharmaceutical compounds when metabolized by these enzymes. In addition, the fact that both compounds act as antiestrogens implies that they may share similar anticancer activities as well as other useful pharmaceutical properties.

In the course of drug development, the inventors observed that treatment of men with isolated trans-clomiphene was accompanied by a clear and significant reduction in IGF-1. Thus, specific derivatives of clomiphene and related triphenylalkylene derivatives represent a class of new cancer therapeutics targeted to the IGF axis. The pharmaceutical properties of these compounds suggest that they represent attractive less toxic alternatives to tamoxifen and other IGF axis targeted therapies.

SUMMARY

In several embodiments, the present invention is related to methods for reducing the level of insulin-like growth factor-1 (IGF-1) in the serum of a subject in need thereof comprising administering to the subject an effective amount of a composition comprising an antiestrogdn or an analog or pharmaceutically acceptable salt thereof. The subject may be a human male or female with a serum IGF-1 level above the normal range, including without limitation, with IGF-1 levels above 300 ng/ml, above 350 ng/ml, above 400 ng/ml or above 500 ng/ml. Preferably the antiestrogen is a selective estrogen receptor modulator (SERM). In a particularly preferred embodiment, a human male with elevated IGF-1 levels is administered a composition comprising trans-clomiphene or an analog or pharmaceutically acceptable salt thereof wherein the composition is substantially free of cis-clomiphene. Preferred trans-clomiphene analogs for use according to the invention are (E)-4-OH-Clomiphene (FIG. 2) and (E)-4-OH-desethyl Clomiphene (FIG. 3).

In related embodiments, the present invention provides a method of treating cancer comprising administering to a subject in need thereof, a composition comprising an effective amount of an antiestrogen or a pharmaceutically acceptable salt thereof. The subject may be a human male or female with elevated serum IGF-1 levels. In a preferred embodiment, the cancer is selected from the group consisting of lung, hepatocellular, breast, renal, gastrointestinal, uterine, ovarian, osteosarcoma and bladder cancer. The antiestrogen may be a SERM and in a particularly preferred embodiment, the composition comprises about 0% to 29% weight/weight of (cis, —Z—, trans-clomiphene) (hereinafter "cis-clomiphene") and about 100% to 71% w/w (trans-, E-, cis-clomiphene) (hereinafter "trans-clomiphene") as active agent or an analog or pharmaceutically acceptable salt thereof. The composition may consist essentially of trans-clomiphene or a salt thereof.

The present invention is also related to a method of treating elevated IGF-1 levels comprising administering to a subject in need thereof, a composition comprising an effective amount of an antiestrogen, preferably a SERM such as trans-clomiphene or an analog or pharmaceutically acceptable salt thereof. The subject may be a human male or female.

The present invention also provides a method for reducing or delaying tumor growth in a subject relative to an untreated subject, comprising administering an IGF-1-reducing amount of a composition comprising an antiestrogen, preferably a SERM such as trans-clomiphene, to the subject. The subject may be a human male or female.

The present invention also provides a method for suppressing the pituitary production of human growth hormone (hGH) comprising administering an effective amount of an antiestrogen, preferably a SERM such as trans-clomiphene or an analog or pharmaceutically acceptable salt thereof, to a subject. The subject may be a human male or female.

The present invention also provides a method for preventing cancer or reducing the risk of cancer in a subject with type 2 diabetes comprising administering to the subject an IGF-1-lowering amount of an antiestrogen, preferably a SERM such as trans-clomiphene or an analog or pharmaceutically acceptable salt thereof. The subject may be a human male or female. Preferably, the antiestrogen is co-administered to the subject with metformin, phenformin, or buformin which act to further reduce the risk of cancer through activation of AMP-activated protein kinase (AMPK) and suppression of mTor.

The present invention also provides a combination therapy whereby a composition comprising an effective amount of an antiestrogen, preferably a SERM such as trans-clomiphene or an analog or pharmaceutically acceptable salt thereof, is sequentially or simultaneously co-administered with one or more additional agents. In some embodiments, the antiestrogen is co-administered with one or more agents designed to further reduce serum IGF-1 levels or IGF-1 signaling through its receptor such as anti-IGF receptor antibodies, IGF receptor-related kinase inhibitors, IGF receptor antisense oligonucleotides or IGF binding protein(s). In other embodiments, the antiestrogen is co-administered with one or more chemopreventive agents that may reduce cancer risk such as metformin, phenformin, or buformin or the like which act through activation of AMPK and suppression of the downstream mTor pathway. In still other embodiments, the antiestrogen is co-administered with one or more chemotherapeutic agents that preferentially target proliferating cells such as a taxane, cisplatin, carboplatin, 5-fluorouracil, irinotecan, topotecan, hydroxyurea, VM-26, vincristine, vinblastine, vinorelbine, cyclophosphamide, doxorubicin, bleomycin and the like.

DETAILED DESCRIPTION

Figure 1:
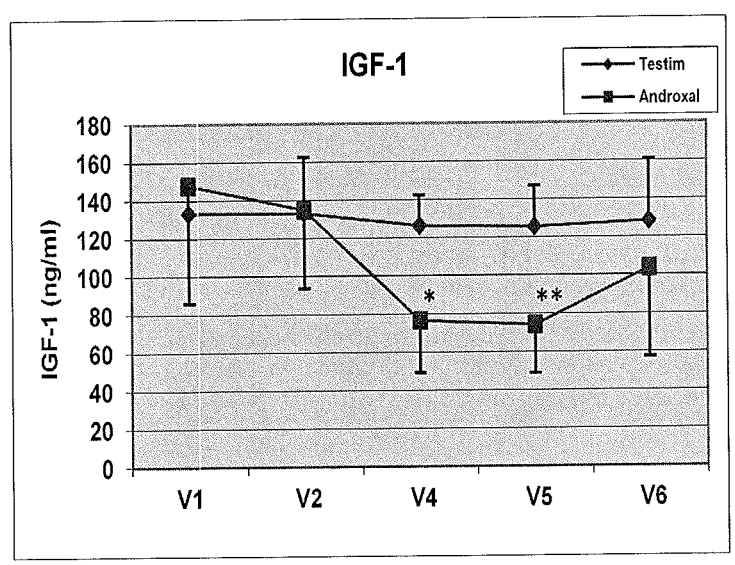
FIG. 1 demonstrates effect of Androxal™ and Testim on total serum IGF-1 levels.

The present invention provides methods for reducing IGF-1 levels in a subject in need of such treatment. The present invention is based on the surprising discovery that trans-clomiphene is useful for significantly reducing the level of serum IGF-1. Clomiphene is thought to exert its effects at the level of the hypothamus-pituitary axis by specifically stimulating secretion of the gonadotropic hormones LH and FSH. Neither of these gonadotropic hormones is known to play a general role in establishment or proliferation of cancer. Studies on the effects of enclomiphine on men found no changes in other hormones secreted by the pituitary such as corticotropin, prolactin or thyroid stimulating hormone. Growth hormone (GH), secreted by the pituitary is known to drive production of IGF-1 by the liver. Without wishing to be bound by theory it is believed that trans-clomiphene suppresses the pituitary production of GH thereby reducing the endocrine stimulated production of liver IGF-1. The activity of trans-clomiphene in reducing serum IGF-1 levels, renders the compositions useful for treating a variety of cancers having strong expression or overexpression of IGF-1 as a common underlying etiology.

Preferably, the compositions are administered to a subject with a serum IGF-1 level above the normal range such as above such as above 250 ng/ml, above 300 ng/ml, above 350 ng/ml, above 400 ng/ml, above 450 ng/ml or above 500 ng/ml. By way of example, the subject may have a serum IGF-1 level between 300 and 1200 ng/ml or any range there between. The normal range of IGF-1 level in a human depends on both age and gender and can be determined e.g. with reference to Friedrich N. et al., Growth Horm. IGF Res., 18(3):228-37 (2008).

Figure 2:
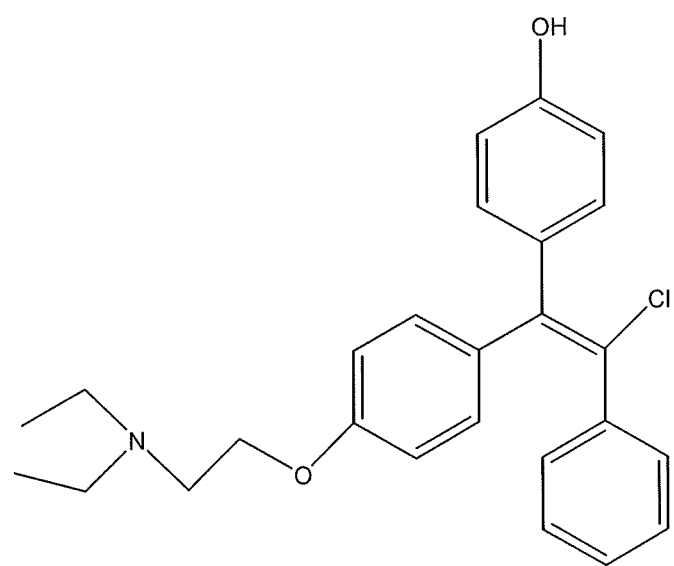
FIG. 2 shows the chemical structure of (E)-4-OH-Clomiphene.
Figure 3:
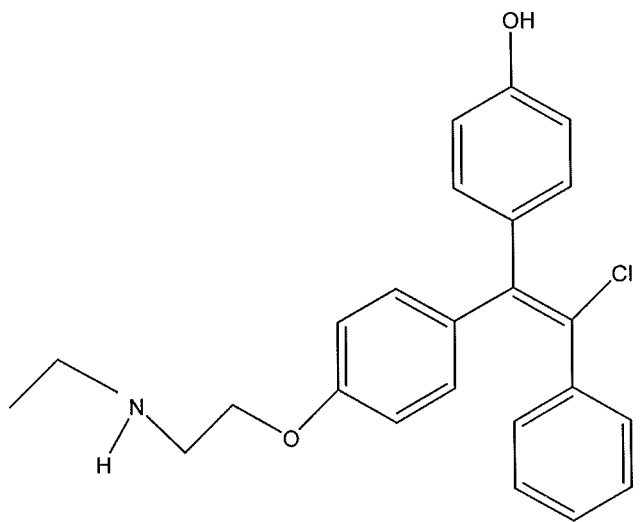
FIG. 3 shows the chemical structure of (E)-4-OH-DE-Clomiphene.
Figure 4:
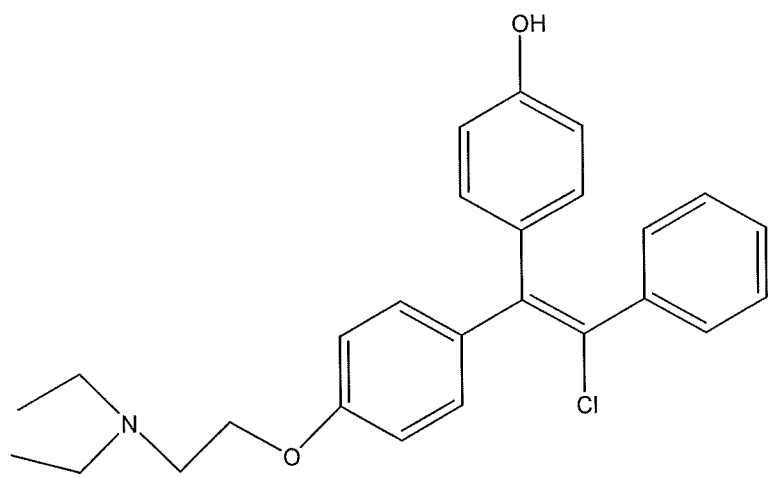
FIG. 4 shows the chemical structure of (Z)-4-OH-Clomiphene.
Figure 5:
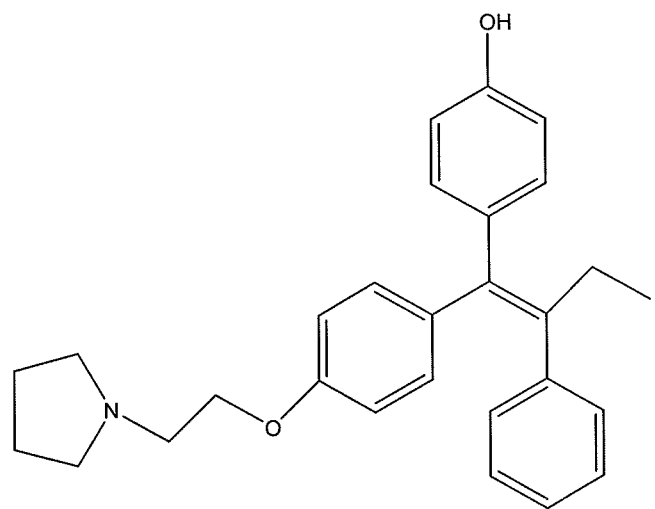
FIG. 5 shows the chemical structure of 4-OH-Pyrrolidinotamoxifen.
Figure 6:
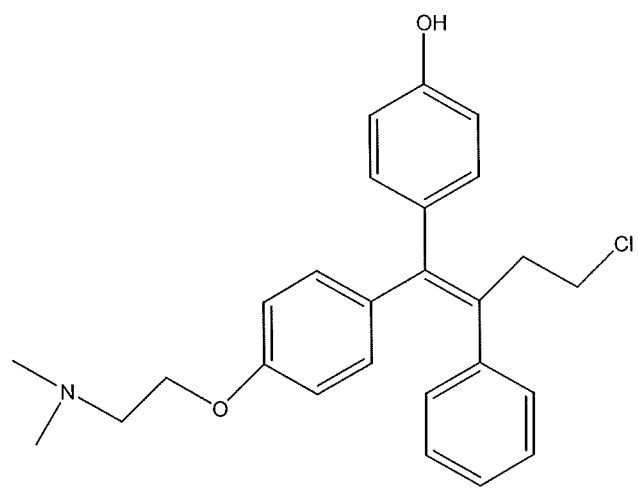
FIG. 6 shows the chemical structure of 4-OH-Toremifene.
Figure 7:
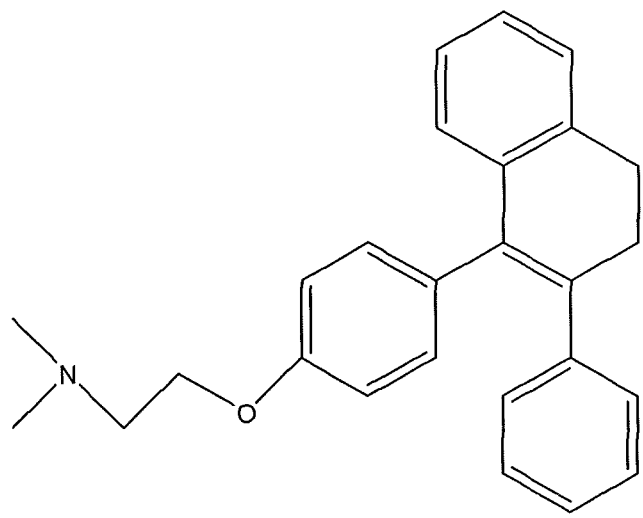
FIG. 7 shows the chemical structure of 4-OH-Fixed Ring Tamoxifen.
Figure 8:
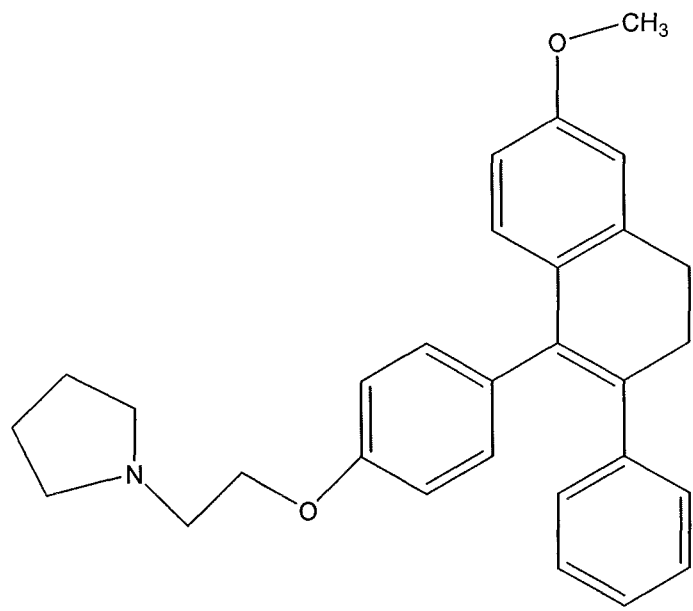
FIG. 8 shows the chemical structure of 4-methoxy-N-diethylated pyrrolidinotamoxifen (nafoxidine).
Figure 9:
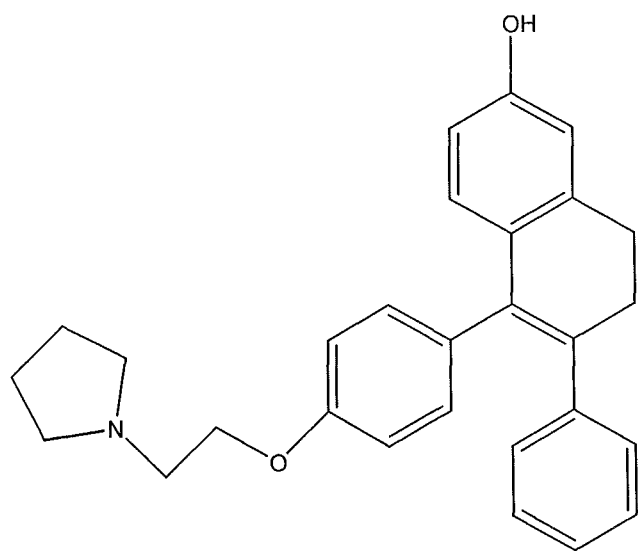
FIG. 9 shows the chemical structure of 4-hydroxyl pyrrolidinotamoxifen.
Figure 10:
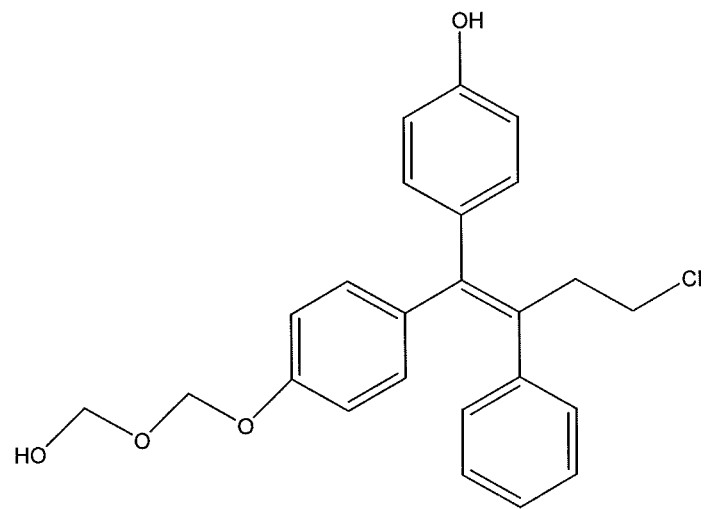
FIG. 10 shows the chemical structure of 4-OH-Fispemifine.

In several embodiments the present invention provides methods for reducing serum IGF-1 levels in a subject and methods for treating cancer in a subject comprising administration of a composition comprising an effective amount of clomiphene or one of its triphenylalkylene analogs. Preferably, the composition consists essentially of trans-clomiphene or a metabolite selected from (E)-4-OH-clomiphene (FIG. 2) and (E)-4-OH-desethyl-clomiphene (FIG. 3). The subject may be a human male or female.

It is to be understood that where the term "cancer" is used herein, this relates to cancer as defined by the National Cancer Institutes' Dictionary of Cancer Terms or any other recognized definition of this syndrome. Synonyms for "cancer" used in the art include; Carcinoma, which is a general term for cancers that begin in the skin or in tissues that line or cover internal organs; Sarcoma, which is a general term of cancers that begin in bone, cartilage, fat, muscle, blood vessels, or other connective or supportive tissue; Leukemia denotes cancers that starts in blood-forming tissue such as the bone marrow; Lymphoma and Multiple Myeloma are cancers that begin in the cells of the immune system. It is to be understood that where the term "cancer" is used herein it also refers to carcinoma, sarcoma, leukemia, lymphoma and multiple myeloma. In addition, cancers are often described by the locus within the body in which they occur. For example, testicular cancer may refer to carcinomas or sarcomas originating in the testes, ovarian cancer may refer to carcinomas of sarcomas originating in the ovaries. Breast cancer may be a carcinoma, sarcoma or lymphoma originating in the breast or mammary tissues. Lung cancers may be carcinomas, sarcomas, lymphomas or multiple myelomas of the lungs.

Cancer cells originating in one portion of the body may migrate to other portions of the body by a process known as metastasis. A tumor formed from cancer cells that have migrated from another part of the body is called a "metastatic tumor" or a "metastatic cancer." In some cases the origin of metastatic tumors or metastatic cancers may be unknown. Metastatic cancer spread throughout the body or it can be narrowly isolated to a single locus or a limited set of loci within the body. Metastatic tumors may have differentiated from one another, or from the source tumor so that they respond differently to particular anticancer treatments.

The term "serum IGF-1" refers to circulating IGF-1 in the serum that is not bound to an IGF binding protein. In this respect it should be understood that the level of serum IGF-1 is dependent on the production of IGF-1 by hepatocytes and the concentration of IGF-1 binding proteins which sequester IGF-1.

The family of triphenylalkylene derivatives representing analogs of clomiphene is defined here to include all unmodified cis and trans forms, as well as each of the 4-hydroxylated, the N-dealkylated and the 4-hydroxy-N-dealkylated analogs of clomiphene, tamoxifen, pyrrolidinotamoxifen, toremifene, fixed ring tamoxifen, fispemifene, as well as all other molecules with substantially similar structures.

In various embodiments of the present invention, administration of a composition comprising an effective amount of an antiestrogen, preferably a SERM such as trans-clomiphene, is used to treat a cancer in a subject with an elevated level of serum IGF-1. The cancer may include, without limitation, carcinomas, sarcomas, leukemias, lymphomas, multiple myelomas whether metastatic or not located in any portion of the body. Preferably, the cancer is characterized by elevated levels of serum IGF-1. The subject may be a human male or female.

In another embodiment of the present invention, administration of a composition comprising an effective amount of an antiestrogen, preferably trans-clomiphene, to a subject with cancer may be combined with any known treatment regimen. In one aspect, the known treatment regimen may target the IGF axis including without limitation medications such as anti-IGF receptor antibodies, IGF receptor related-kinases, and IGF receptor antisense oligonucleotides. In other aspects, the known treatment regimen may comprise one or more chemotherapeutic agents that preferentially target cancer cells. In this respect, it known that cancer cells can produce IGF-1 which acts in an autocrine/paracrine fashion. Thus co-administration of a cancer cell-targeting chemotherapeutic agent with a composition of the invention provides a mechanism for reducing both endocrine and autocrine/paracrine IGF-1. Such cancer cell-targeting chemotherapeutic agents include, without limitation, chemotherapies targeting the EGF axis, or estrogen receptor medicants, alkylating drugs such as cyclophosphamide, antimetabolites such as 5-flurouracil, antitumor antibiotics such as bleomycin, plant alkaloids such as vinbastine, topoisomerase inhibitors such as etoposide, immunotherapies and the like. In addition, such compositions may prove effective in association with radiation therapies targeted against cancers. Compositions of the invention may be simultaneously, separately or sequentially administered with any of the aforementioned known treatment regimens.

In another embodiment of the present invention, administration of a composition comprising an effective amount of an antiestrogen is used to treat elevated levels of IGF-1 in a subject. The subject may be male or female.

In another embodiment of the present invention, a patient with cancer and an elevated serum level of IGF-1 levels is administered a composition comprising an effective amount of an antiestrogen, preferably trans-clomiphene. Whether a patient has an elevated serum level of IGF-1 is determined with reference to the patient's age and gender as described above. In various embodiments, the cancer patient may an IGF-1 level above about 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050 or 1060 ng/ml. In a preferred embodiment, the cancer patient has an IGF level above the normal range for example, above 300, 350, 400, 450, 500, 550, 600, 650, 700, 750, 800, 850, 900, 950, 1000, 1050 ng/ml or any range therebetween such as between 300-1050, 400-1050 or 500-1050 ng/ml. The composition may comprise an amount of an antiestrogen, preferably trans-clomiphene, effective to lower the cancer patient's IGF-1 level into the normal range for example, below about 500, 400, 300, 250, or 200 ng/ml.

In some embodiments, the subject in need of treatment by any of the methods of the present invention is a secondary hypogonadal male. In related embodiments, the subject in need of treatment by any of the methods of the present invention is a human male with a body mass index of at least 20, at least 21, at 22, at least 23, at least 24, at least 25, at least 26, at least 27, at least 28, at least 29, at least 30, at least 31 or at least 32. For example, the subject in need of treatment may be a human male with a body mass index of at least 25.

In related embodiments, the subject in need of treatment by any of the methods of the present invention is a human male or female with type 2 diabetes in which case the compositions of the invention are preferentially administered as part of a dosage regimen designed to reduce the risk of cancer. In preferred embodiment, the subject is a human male with type 2 diabetes and the antiestrogen, preferably a SERM such as trans-clomiphene, is co-administered sequentially or simultaneously to the subject with metformin, phenformin, or buformin.

In a preferred embodiment of the present invention, a patient with a single cancer or metastasizing cancers and an elevated serum IGF-1 level is administered one or more dosages of an effective amount of a composition comprising trans-clomiphene at a dosage between one mg to about 200 mg (although the determination of optimal dosages is within the level of ordinary skill in the art) in order to treat the cancer. Cis-clomiphene may also be present in the composition so long as the ratio of trans-clomiphene to cis-clomiphene is greater than 71/29. Analogs of the trans- and cis-isomers of clomiphene such as those described in Ernst, et al. supra and the metabolites described herein are also useful in the practice of the present invention.

An "effective amount" of the antiestrogen is defined as an amount effective to lower IGF-1 levels in a subject below a baseline level prior to initiation of treatment. Preferably, compositions of the invention are effective to lower IGF-1 levels in a subject by at least 5%, at least 10%, at least 15%, at least 20%, at least 25%, at least 30%, at least 35% or at least 40% over the course of the treatment. For example, the compositions may be effective to lower serum IGF-1 levels in a subject by between 15% and 40%. Preferably, the compositions are effective to reduce serum IGF-1 levels into the normal range with respect to the subject's gender and age during the course of administration for example with reference to the Mayo Clinic Reference Values for IGF-1 [available at www.mayomedicallaboratories.com/test-catalog/Clinical+and+Interpretive/83357, last accessed Oct. 22, 2012]. Compositions of the invention may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al., Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art. A preferred antiestrogen for use in the methods of the invention is trans-clomphene an effective dose of which may range from 1 to 200 mg or from 5 to 100 mg. The dosage of trans-clomphene may also be from 12.5 to 50 mg. The dosage of trans-clomphene may also be 12.5 mg, 25 mg or 50 mg.

The terms "treat" or "treatment" as used in the instant application, refer to both therapeutic treatment and prophylactic or preventative measures, wherein the object is to prevent or slow down (lessen) an undesired physiological or psychological change or disorder, such as conditions associated with cancer. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

The terms "modulate" or "modulating", as used in the instant application, refer to both therapeutic treatment and prophylactic or preventative measures, wherein the object is to prevent or slow down (lessen) an undesired clinical parameter. For purposes of the present invention, beneficial or desired clinical results include, but are not limited to, correcting of clinical parameter, diminishment of extent of clinical parameter, stabilized (i.e., not worsening) clinical parameter and delay or slowing of extent of clinical parameter.

By "antiestrogen" it is meant a compound that prevents estrogens from expressing their effects on estrogen dependent target tissues consequently antagonizing a variety of estrogen-dependent processes. Based on the unexpected finding that the antiestrogenic trans-clomiphene isomer is useful in reducing serum IGF-1 levels, it is expected that other compounds with antiestrogenic activity will be useful in the present invention. In all cases, antiestrogens useful in the practice of the instant invention are those capable of reducing IGF-1 levels in a mammal. Without wishing to be bound by theory, it is believed that administration of antiestrogens will result in reducing IGF-1 levels by blocking growth hormone driven hepatic production of endocrine IGF-1.

Antiestrogens useful in the practice of the instant invention may be pure antiestrogens or may have partial estrogenic action as in the case of the selective estrogen receptor modulators (SERMs) which exhibit antiestrogenic properties in some tissues and estrogenic tissues in others.

SERMs of the invention include, without limitation, triphenylalkylenes, which include: 2-[4-(1,2-diphenylbut-1-enyl)phenoxy]-N,N-dimethyl-ethanamine (tamoxifen) and other compounds described in U.S. Pat. No. 4,536,516, incorporated herein by reference; 4'-hydroxy-2-[4-(1,2-diphenylbut-1-enyl)phenoxy]-N,N-dimethyl-ethanamine (4'-hydroxytamoxifen) and other compounds described in U.S. Pat. No. 4,623,660, incorporated herein by reference, as well as the dealkylated variant 4'-hydroxy-2-[4-(1,2-diphenylbut-1-enyl)phenoxy]-N-monomethyl-ethanamine (N-desmethyl-4'-hydroxytamoxifen also known as endoxifen); fixed ring tamoxifen and its 4'-hydroxyl, N-desmethyl, N-desethyl, 4'-hydroxy-N-desmethyl and 4'-hydroxy-N-desethyl forms; 1-[4'-(dimethylaminoethoxy)phenyl]-1-(3'-hydroxyphenyl)-2-phenylbut-1-ene (droloxifene) and other compounds described in U.S. Pat. No. 5,047,431 as well as their 4'-hydroxy, N-desethyl and 4'-hydroxy-N-desethyl forms; 2-[p-[4-chloro-1,2-diphenyl-1-butenyl]phenoxy]-N,N-dimethylethylamine (toremifene) and other compounds described in U.S. Pat. Nos. 4,696,949, 5,491,173 and 4,996,225, each of which is incorporated herein by reference, as well as 4'-hydroxytoremifene, N-desmethyl-toremifene and N-desmethyl-4'-hydroxytoremifene; 1-(2-(4-(1-(4-iodophenyl)-2-phenyl-but-1-enyl)-phenoxy)-ethyl)-pyrrolidinone (idoxifene) and other compounds described in U.S. Pat. No. 4,839,155, incorporated herein by reference; as well as 4-hydroxypyrrolidinotamoxifene; 2-(2-{4-[(1Z)-4-chloro-1,2-diphenylbut-1-en-1-yl]phenoxy}ethoxy)ethan-1-ol (fispemifene) and other compounds described in U.S. Pat. No. 7,504,530, each of which is incorporated herein by reference, as well as 4'-hydroxyfispemifene; clomiphene and both its isomers; and compounds described in U.S. Pat. Nos. 4,696,949 and 5,491,173 and 6,576,645, each of which is incorporated herein by reference, as well as (E) 4'-hydroxyclomiphene, (E) N-desethyl-clomiphene and (E) N-desethyl-4'-hydroxyclomiphene.

SERMS of the invention also include, without limitation, benzothiphene derivatives such as: [6-hydroxy-2-(4-hydroxyphenyl)-benzothiophen-3-yl]-[4-[2-(1-piperidinyl)ethoxy)phenyl]-methanone (raloxifene) and other compounds described in U.S. Pat. Nos. 4,418,068 and 5,393,763, both of which are incorporated herein by reference; LY353381; and LY335563 and other compounds described in WO 98/45286, WO 98/45287 and WO 98/45288; benzopyran derivatives such as: (+)-7-pivaloyloxy-3-(4'pivaloyloxyphenyl)-4-methyl-2-(4"-(2"piperidinoethoxy)phenyl)-2H-benzopyran (EM 800/SCH 57050) and other compounds described in WO 96/26201; (2S)-3-(4-hydroxyphenyl)-4-methyl-2-[4-[2-(1-piperidyl)ethoxy]phenyl]-2H-chromen-7-ol (EM 652); naphthalene derivatives such as: Cis-6-phenyl-5-[4-(2-pyrrolidin-1-yl-ethoxy)-phenyl]-5,6,7,8-tetrahydronaphthalen-2-ol (lasofoxifene/CP 336,156) and other compounds described in U.S. Pat. No. 5,552,412; 3,4-dihydro-2-(p-methoxyphenyl)-1-naphthyl-p-[2-(1-pyrrolidinyl)ethoxy]phenyl ketone (trioxifene/LY133314) and other compounds described in U.S. Pat. No. 4,230,862, incorporated herein by reference; and 1-(4-Substituted alkoxy)benzyl)naphthalene compounds such as those described in U.S. Pat. No. 6,509,356, incorporated herein by reference; chromans such as 3,4-trans-2,2-dimethyl-3-phenyl-4-[4-(2-(2-(pyrrolidin-1-yl)ethoxy)phenyl]-7-methoxychroman (levormeloxifene) and other compounds described in WO 97/25034, WO 97/25035, WO 97/25037 and WO 97/25038; and 1-(2-((4-(-methoxy-2,2, dimethyl-3-phenyl-chroman-4-yl)-phenoxy)-ethyl)-pyrrolidine (centchroman) and other compounds described in U.S. Pat. No. 3,822,287, incorporated herein by reference.

Other SERMs of the invention include, without limitation, the compounds described in U.S. Pat. Nos. 6,387,920, 6,743,815, 6,750,213, 6,869,969, 6,927,224, 7,045,540, 7,138,426, 7,151,196, and 7,157,604, each of which is incorporated herein by reference.

Further non-limiting antiestrogens of the invention include: 6α-chloro-16α-methyl-pregn-4-ene-3,20-dione (clometherone); 6-chloro-17-hydroxypregna-1,4,6-triene-3,20-dione (delmadinone); 1-[2-[4-[1-(4-methoxyphenyl)-2-nitro-2-phenylethenyl]phenoxy]ethyl]-pyrrolidine (nitromifene/CN-55,945-27); and 1-[2-[p-(3,4-Dihydro-6-methoxy-2-phenyl-1-naphthyl)phenoxy]ethyl]pyrrolidine (nafoxidene).

Further non-limiting antiestrogens of the invention include indoles such as those disclosed in J. Med. Chem., 33:2635-2640 (1990), J. Med. Chem., 30:131-136 (1987), WO 93/10741, WO 95/17383, WO 93/23374 and U.S. Pat. Nos. 6,503,938 and 6,069,153, both of which are incorporated herein by reference.

Further non-limiting antiestrogens of the invention include 2-[3-(1-cyano-1-methyl-ethyl)-5-(1H-1,2,4-triazol-1-ylmethyl)phenyl]-2-methyl-propanenitrile (anastrozole) and other compounds described in EP 0296749; 6-Methylenandrosta-1,4-diene-3,17-dione (exemestane) and other compounds described in U.S. Pat. No. 4,808,616, incorporated herein by reference; 4-[(4-cyanophenyl)-(1,2,4-triazol-1-yl)methyl]benzonitrile (letrozole) and other compounds described in U.S. Pat. No. 5,473,078, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2α,3α-Epithio-5α-androstan-17β-01 (epitiostanol); 2α,3α-Epitio-5α-androstane-17β-yl-1-methoxycyclopentyloxy (mepitiostane); 4-[(2Z,4Z)-4-(4-hydroxyphenyl)hexa-2,4-dien-3-yl]phenol (cycladiene) and other compounds described in U.S. Pat. Nos. 2,464,203 and 2,465,505, both of which are incorporated herein by reference; CI-680 described in Unlisted Drugs, 28(10): 169(0) (1976); CI-628 described in Unlisted Drugs, 26(7): 106(1) (1974); 13-ethyl-17α-ethynl-17β-hydroxygona-4,9,1-trien-3-one (R2323); diphenol hydrochrysene and erythryo-MEA both described in Geynet, et al., Gynecol. Invest. 3(1):2-29 (1972); 1-[1-chloro-2,2-bis(4-methoxyphenyl)ethenyl]-4-methoxy-benzene (chlorotrianisene) described in Merck Index, 10$^{th}$ ed., #2149; 1-[4-(2-Diethylaminoethoxyl)phenyl]-1-phenyl-2-(p-anisyl)ethanol (ethamoxytriphetol) described in Merck Index, 10$^{th}$ ed., #3668; and 2-p-Chlorophenyl-[4p-(2-diethylaminoethoxyl)phenyl]-1-p-tolylethanol (triparanol) and other compounds described in U.S. Pat. No. 2,914,562, incorporated herein by reference.

Still other antiestrogens of the invention include, without limitation: (2e)-3-(4-((1e)-1,2-diphenylbut-1-enyl)phenyl) acrylic acid (GW5638), GW7604 and other compounds described in Wilson et al., Endocrinology, 138(9):3901-3911 (1997) and WO 95/10513; 1-[4-(2-diethylaminoethoxyl) phenyl]-2-(4-methoxyphenyl)-1-phenyl-ethanol (MER-25), N,N-diethyl-2-[4-(5-methoxy-2-phenyl-3H-inden-1-yl)phenoxy]ethanamine hydrochloride (U-11,555A), 1-[2-[4-(6-methoxy-2-phenyl-3,4-dihydronaphthalen-1-yl)phenoxy]ethyl]pyrrolidine hydrochloride (U-11,100A), ICI-46,669, 2-[4-[(Z)-1,2-diphenylbut-1-enyl]phenoxy]-N,N-dimethyl-ethanamine; 2-hydroxypropane-1,2,3-tricarboxylic acid (ICI-46,474) and other compounds described in Terenius et al., Gynec. Invest., 3:96-107 (1972); 2-Hydroxy-6-naphthalenepropionic acid (allenolic acid); [4-[(4-acetyloxyphenyl)-cyclohexylidene-methyl]phenyl]acetate (cyclofenyl/ICI-48213); [6-hydroxy-2-(4-hydroxyphenyl)benzothiophen-3-yl]-[4-[2-(1-piperidyl)ethoxy]phenyl]methanone (keoxifene); 4-[(Z)-1-[4-(2-dimethylaminoethoxyl)phenyl]-2-(4-propan-2-ylphenyl)but-1-enyl]phenol (DP-TAT-59/miproxifene); (1RS,2RS)-4,4'-diacetoxy-5,5'-difluoro-(1-ethyl-2-methylene)di-m-phenylenediacetate (acefluranol); 6-hydroxy-2-(p-hydroxyphenyl)-benzo(b)thien-3-yl[2-(1-pyrrolidinyl)-ethoxyphenyl]ketone (LY-117018); and [6-hydroxy-2-(4-hydroxy-phenyl)benzo(b)thien-3-yl]-[4-(2-(1-piperidinyl)-ethoxy)phenyl]methanone (LY-156758).

Still other antiestrogens of the invention include, without limitation: non-steroidal estrogen receptor ligands such as those described in U.S. Pat. Nos. 5,681,835, 5,877,219, 6,207,716, 6,340,774 and 6,599,921, each of which is incorporated herein by reference; steroid derivatives such as those described in U.S. Pat. No. 4,659,516, incorporated herein by reference; 7α-11-aminoalkyl-estratrienes such as those described in WO 98/07740; 11-β-halogen-7α-substituted estratrienes such as those described in WO 99/33855; 17α-alkyl-17β-oxy-estratrienes such as those described in U.S. patent application Ser. No. 10/305,418, incorporated herein by reference; 2-phenyl-1-[4-(2-aminoethoxy)-benzyl]-indoles such as those described in U.S. Pat. No. 7,132,417, incorporated herein by reference; 4-fluoroalkyl-2h-benzopryans such as those described in U.S. Pat. No. 6,844,336, incorporated herein by reference; (4-(2-(2-aza-bicyclo[2.2.1]hept-2-yl)-ethoxy)-phenyl)-(6-hydroxy-2-(4-hydroxy-phenyl)-benzo[b]thiop hen-3-yl)-methanone and other benzothiophenes described in WO 95/10513 and U.S. Pat. No. 4,133,814, incorporated herein by reference; 2-phenyl-1-[4-(2-aminoethoxy)-benzyl]-indoles such as those described in U.S. Pat. No. 5,998,402, incorporated herein by reference; 3-[4-(2-Phenyl-Indole-1-ylmethyl) Phenyl]-Acrylamides and other compounds described in U.S. Pat. No. 5,985,910, incorporated herein by reference; 2-phenyl-1-[4-(amino-1-yl-alk-1-ynyl)-benzyl]-1H-indol-5-ols and other compounds described in U.S. Pat. Nos. 5,780,497 and 5,880,137, both of which are incorporated herein by reference; steroids such as those described in U.S. Pat. Nos. 6,455,517, 6,548,491, 6,747,018 and 7,041,839, each of which is incorporated herein by reference; Di-(3'-hydroxyphenyl)-alkane compounds such as those described in U.S. Pat. No. 4,094,994, incorporated herein by reference; phenol derivatives such as those described in U.S. Pat. No. 4,751,240, incorporated herein by reference; 2,3-diaryl-2H-1-benzopyran analogs such as those described in Saeed et al., J. Med. Chem., 33:3210-3216 (1990) and Sharma et al., J. Med. Chem. 33:3216-3229 (1990); and benzofuran and triarylfuran analogs such as those described in Durani et al., J. Med. Chem., 32:1700-1707 (1989).

In one embodiment, compositions of the invention comprise one or more pharmaceutically acceptable salts of an antiestrogen. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbensenesulfonic acid, toluenesulfonic acid, galactaric acid, galacturonic acid or naphthalenesulfonic acid. All crystalline form polymorphs may be used in accordance with the invention. A preferred salt is the citrate salt.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like.

Compositions of the instant invention can be prepared in the form of a dose unit or dose units suitable for oral, parenteral, transdermal, rectal, transmucosal, or topical administration. Parenteral administration includes, but is not limited to, intravenous, intraarterial, intraperitoneal, subcutaneous, intramuscular, intrathecal, and intraarticular.

The teems "oral administration" or "orally deliverable" herein include any form of delivery of a therapeutic agent or a composition thereof to a subject wherein the agent or composition is placed in the mouth of the subject, whether or not the agent or composition is swallowed. Thus, "oral administration" includes buccal and sublingual as well as esophageal (e.g. inhalation) administration.

In still another embodiment, compositions of the present invention are formulated as rectal suppositories, which may contain suppository bases including, but not limited to, cocoa butter or glycerides.

Compositions of the present invention may also be formulated for inhalation, which may be in a form including, but not limited to, a solution, suspension, or emulsion that may be administered as a dry powder or in the form of an aerosol using a propellant, such as dichlorofuoromethane or trichlorofluoromethane.

Compositions of the present invention may also be formulated for transdermal delivery, for example as a cream, ointment, lotion, paste, gel, medicated plaster, patch, or membrane. Such compositions can comprise any suitable excipients, for example penetration enhancers and the like.

Compositions of the present invention may also be formulated for parenteral administration including, but not limited to, by injection or continuous infusion. Formulations for injection may be in the form of suspensions, solutions, or emulsions in oily or aqueous vehicles. Such compositions may also be provided in powder form for reconstitution with a suitable vehicle including, but not limited to, sterile, pyrogen-free water, WFI, and the like.

Compositions of the present invention may also be formulated as a depot preparation, which may be administered by implantation or by intramuscular injection. Such compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. Liposome preparations can comprise liposomes which penetrate the cells of interest or the stratum corneum and fuse with the cell membrane resulting in delivery of the contents of the liposome into the cell. For example, liposomes such as those described in U.S. Pat. No. 5,077,211 to Yarosh, U.S. Pat. No. 4,621,023 to Redziniak et al., or U.S. Pat. No. 4,508,703 to Redziniak et al. can be used.

A composition of the invention can be in the form of solid dosage units such as tablets, (e.g. suspension tablets, bite suspension tablets, rapid dispersion tablets, chewable tablets, effervescent tablets, bilayer tablets, etc.), caplets, capsules (e.g., a soft or hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for administration. A preferable dosage form is a soft or hard gelatin capsule.

Tablets can be prepared according to any of the many relevant, well known pharmacy techniques. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms can be prepared by mixing an antiestrogen with one or more pharmaceutical excipients to form a substantially homogenous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the invention. The term "compressed tablet" generally refers to a plain, uncoated tablet suitable for oral ingestion, prepared by a single compression or by pre-compaction tapping followed by a final compression. Tablets of the present invention may be coated or otherwise compounded to provide a dosage form affording the advantage of improved handling or storage characteristics. In one embodiment, any such coating will be selected so as to not substantially delay onset of therapeutic effect of a composition of the invention upon administration to a subject. The term "suspension tablet" as used herein refers to a compressed tablet that rapidly disintegrates after placement in water.

Suitable liquid dosage forms of a composition of the invention include solutions, aqueous or oily suspensions, elixirs, syrups, emulsions, liquid aerosol formulations, gels, creams, ointments, etc. Such compositions may also be formulated as a dry product for constitution with water or other suitable vehicle before use.

In one embodiment, liquid or semi-solid compositions, upon storage in a closed container maintained at either room temperature, refrigerated (e.g. about 5-10 C) temperature, or freezing temperature for a period of about 1, 2, 3, 4, 5, 6, 7, 8, 9, 10, 11, or 12 months, exhibit at least about 90%, at least about 92.5%, at least about 95%, or at least about 97.5% of the original antiestrogen compound present therein.

Compositions of the invention can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition. Excipients include, by way of illustration and not limitation, diluents, disintegrants, binding agents, adhesives, wetting agents, lubricants, glidants, surface modifying agents or surfactants, fragrances, suspending agents, emulsifying agents, nonaqueous vehicles, preservatives, antioxidants, adhesives, agents to adjust pH and osmolarity (e.g. buffering agents), preservatives, thickening agents, sweetening agents, flavoring agents, taste masking agents, colorants or dyes, penetration enhancers and substances added to improve appearance of the composition.

Excipients optionally employed in compositions of the invention can be solids, semi-solids, liquids or combinations thereof. Compositions of the invention containing excipients can be prepared by any known technique of pharmacy that comprises mixing an excipient with a drug or therapeutic agent.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, about 10% to about 85%, or about 20% to about 80%, of the total weight of the composition. Any diluent or diluents selected preferably exhibit suitable flow properties and, where tablets are desired, compressibility.

The use of extragranular microcrystalline cellulose (that is, microcrystalline cellulose added to a wet granulated composition after a drying step) can be used to improve hardness (for tablets) and/or disintegration time.

Compositions of the invention optionally comprise one or more pharmaceutically acceptable disintegrants as excipients, particularly for tablet, capsule or other solid formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, constitute in total about 0.2% to about 30%, about 0.2% to about 10%, or about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICD, propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. One or more anti-adherents, if present, constitute about 0.1% to about 10%, about 0.25% to about 5%, or about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Compositions of the present invention can comprise one or more anti-foaming agents. Simethicone is an illustrative anti-foaming agent. Anti-foaming agents, if present, constitute about 0.001% to about 5%, about 0.001% to about 2%, or about 0.001% to about 1%, of the total weight of the composition.

Illustrative antioxidants for use in the present invention include, but are not limited to, butylated hydroxytoluene, butylated hydroxyanisole, potassium metabisulfite, and the like. One or more antioxidants, if desired, are typically present in a composition of the invention in an amount of about 0.01% to about 2.5%, for example about 0.01%, about 0.05%, about 0.1%, about 0.5%, about 1%, about 1.5%, about 1.75%, about 2%, about 2.25%, or about 2.5%, by weight.

In various embodiments, compositions of the invention can comprise a preservative. Suitable preservatives include, but are not limited to, benzalkonium chloride, methyl, ethyl, propyl or butylparaben, benzyl alcohol, phenylethyl alcohol, benzethonium, methyl or propyl p-hydroxybenzoate and sorbic acid or combinations thereof. Typically, the optional preservative is present in an amount of about 0.01% to about 0.5% or about 0.01% to about 2.5%, by weight.

In one embodiment, compositions of the invention optionally comprise a buffering agent. Buffering agents include agents that reduce pH changes. Illustrative classes of buffering agents for use in various embodiments of the present invention comprise a salt of a Group IA metal including, for example, a bicarbonate salt of a Group IA metal, a carbonate salt of a Group IA metal, an alkaline or alkali earth metal buffering agent, an aluminum buffering agent, a calcium buffering agent, a sodium buffering agent, or a magnesium buffering agent. Suitable buffering agents include carbonates, phosphates, bicarbonates, citrates, borates, acetates, phthalates, tartrates, succinates of any of the foregoing, for example sodium or potassium phosphate, citrate, borate, acetate, bicarbonate and carbonate.

Non-limiting examples of suitable buffering agents include aluminum, magnesium hydroxide, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in The Merck Index, Merck & Co. Rahway, N.J. (2001)). Furthermore, combinations or mixtures of any two or more of the above mentioned buffering agents can be used in the pharmaceutical compositions described herein. One or more buffering agents, if desired, are present in compositions of the invention in an amount of about 0.01% to about 5% or about 0.01% to about 3%, by weight.

In various embodiments, compositions the invention may include one or more agents that increase viscosity. Illustrative agents that increase viscosity include, but are not limited to, methylcellulose, carboxymethylcellulose sodium, ethylcellulose, carrageenan, carbopol, and/or combinations thereof. Typically, one or more viscosity increasing agents, if desired, are present in compositions of the invention in an amount of about 0.1% to about 10%, or about 0.1% to about 5%, by weight.

In various embodiments, compositions of the invention comprise an "organoleptic agent" to improve the organoleptic properties of the composition. The term "organoleptic agent" herein refers to any excipient that can improve the flavor or odor of, or help mask a disagreeable flavor or odor of a composition of the invention. Such agents include sweeteners, flavoring agents and/or taste masking agents. Suitable sweeteners and/or flavoring agents include any agent that sweetens or provides flavor to a pharmaceutical composition. Optional organoleptic agents are typically present in a composition of the invention in an amount of about 0.1 mg/ml to about 10 mg/ml, about 0.5 mg/ml to 5 mg/ml or about 1 mg/mi.

Illustrative sweeteners or flavoring agents include, without limitation, acacia syrup, anethole, anise oil, aromatic elixir, benzaldehyde, benzaldehyde elixir, cyclodextrins, caraway, caraway oil, cardamom oil, cardamom seed, cardamom spirit, cardamom tincture, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, *glycyrrhiza, glycyrrhiza* elixir, *glycyrrhiza* extract, *glycyrrhiza* extract pure, *glycyrrhiza* fluid extract, *glycyrrhiza* syrup, honey, iso-alcoholic elixir, lavender oil, lemon oil, lemon tincture, mannitol, methyl salicylate, nutmeg oil, orange bitter, elixir, orange bitter, oil, orange flower oil, orange flower water, orange oil, orange peel, bitter, orange peel sweet, tincture, orange spirit, orange syrup, peppermint, peppermint oil, peppermint spirit, peppermint water, phenylethyl alcohol, raspberry juice, raspberry syrup, rosemary oil, rose oil, rose water, stronger, saccharin, saccharin calcium, saccharin sodium, sarsaparilla syrup, sarsaparilla, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Illustrative taste masking agents include, but are not limited to, cyclodextrins, cyclodextrins emulsions, cyclodextrins particles, cyclodextrins complexes, or combinations thereof.

Illustrative suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats.

Illustrative emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol.

The foregoing excipients can have multiple roles as is known in the art. For example, starch can serve as a filler as well as a disintegrant. The classification of excipients above is not to be construed as limiting in any manner.

Compositions of the present invention may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, intraarticular, intracisternal and intraventricular.

A therapeutically effective amount of the composition required for use in therapy varies with the length of time that activity is desired, and the age and the condition of the patient to be treated, among other factors, and is ultimately determined by the attendant physician. In general, however, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a composition of the invention may be administered to a subject to provide the subject with an antiestrogen in an amount of about 1 µg/kg to about 1 mg/kg body weight, for example about 1 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µs/kg, about 825 µg/kg, about 850 µg/kg, about 875 µg/kg, about 900 µg/kg, about 925 µg/kg, about 950 µg/kg, about 975 µg/kg or about 1 mg/kg body weight.

In a preferred embodiment, compositions according to the present invention comprise trans-clomiphene at a dosage between one mg to about 200 mg (although the determination of optimal dosages is with the level of ordinary skill in the art). The composition may comprise trans-clomiphene at a dosage of about 1 mg, 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between. The composition may also comprise trans-clomiphene and cis-clomiphene at a ratio of about 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.5/0.5 or there between. Analogs of the trans- and cis-isomers of clomiphene such as those described in Ernst, et al. supra are also useful in the practice of the present invention.

Compositions of the present invention may also be administered long-term. In this regard, the compositions may be administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The compositions may also be administered for an administration period of at least 1, 2, 3, 4, 5, 6, 7, 8, 9, 10, 11, 12 or more months. The compositions may also be administered for an administration period of at least 1, 2, 3, 4, 5, 6, 7 8, 9, 10 or more years. During the administration period, the composition may be administered daily or periodically such as every other day and the like.

Compositions of the present invention may also be administered intermittently. For example, the compositions may be administered for an administration period of 1, 2, 3, 4, 5, or more weeks, followed by a period of discontinuance, followed by an administration period of 1, 2, 3, 4, 5 or more weeks, and so on.

All of the references referred to herein are incorporated by reference in their entirety.

The following Examples are meant to be illustrative of the invention and are not intended to limit the scope of the invention as set out is the appended claims.

EXAMPLE 1

Effects of Trans-Clomiphene and Exogenous Testosterone Treatment on Free Serum IGF-1

The effect of the isolated trans-clomiphene isomer on free serum IGF-1 was tested in three separate clinical studies.

Adult male subjects with a morning total testosterone blood level of <300 ng/dl and a serum LH of <15 IU/ml who had previously undergone between 6 months and two years of topical testosterone therapy were administered either trans-clomiphene (25 mg/day via oral capsule) or a topical testosterone gel (Testim®, 50 mg applied daily) over a six month period according to the first study. Following an initial screening visit (Visit 1-V1), topical testosterone replacement therapy in the subjects was discontinued for either three weeks or three months. At the end of the washout period (Visit 2-V2), quantitative determination of baseline serum (circulating) IGF-1 measurements were made in the subjects by immunoenzymometric assay (Immunodiagnostics Systems Ltd., OCTEIA® IGF-1 kit) and treatment with either trans-clomiphene or Testim® was initiated. Follow-up measurements were taken at 3 months post initial dose (Visit 4-V4), 6 months post initial dose (Visit 5-V5) and one month after cessation of treatment (Visit 6-V6). Seven subjects completed six months of trans-clomiphene therapy and five subjects completed six months of Testim® therapy. The results are presented at FIG. 1. At baseline (V2), serum IGF-1 levels in both patient groups averaged about 140 ng/ml. After 3 months of treatment (V4), serum IGF-1 levels were significantly reduced in the trans-clomiphene group to below 80 ng/ml; no corresponding reduction was observed in the Testim® group. IGF-1 levels remained depressed in the trans-clomiphene group after 6 months of treatment (V5); the Testim® group again exhibited no change in IGF-1 at the 6 month time point. Thus, circulating serum IGF-1 levels were reduced over 40% in subjects administered trans-clomiphene whereas exogenous testosterone had no effect on circulating serum IGF-1. Importantly, aside from low testosterone, these subjects were otherwise healthy—thus, administering trans-clomiphene provides an effective method for reducing serum levels of IGF-1 produced by the liver (i.e. growth-hormone dependent IGF-1).

Another study measured serum IGF-1 levels in human males with low/low-normal testosterone following treatment with trans-clomiphene. Briefly 38 males were administered trans-clomiphene at 12.5 mg per day, 35 males were administered trans-clomiphene at 25 mg per day and 43 males were administered a placebo (control group). Serum IGF-1 levels were measured by immunoenzymometric assay as described above at baseline and following three months of treatment with trans-clomiphene or placebo for each treatment group. The results are presented in Table 1 below and demonstrate a ~32% mean reduction in serum IGF-1 levels for the 12.5 mg group and a 36% mean reduction for the 25 mg group.

TABLE 1

| Treatment Group (n = number of subjects) | Baseline IGF-1 µg/L (st dev) | Month 3 IGF-1 µg/L (st dev) | Mean Change from Baseline µg/L (st dev) | P-value (vs Placebo) |
|---|---|---|---|---|
| 12.5 mg (n = 38) | 115.2 (35.11) | 77.3 (30.8) | −36.8 (22.3) | <0.0001 |
| 25 mg (n = 35) | 107.2 (39.4) | 70.4 (38.6) | −38.3 (29.5) | <0.0001 |
| Placebo (n = 43) | 113.6 (45.4) | 107.0 (47.4) | −8.5 (27.9) | |

In a third study, the effect of three doses of trans-clomiphene (6.5 mg, 12.5 mg and 25 mg, each administered daily) on IGF-1 levels relative to baseline were compared to Androgel (administered daily). Briefly, human males testosterone levels not greater than 350 ng/dl (average age=53.1; average BMI=31.8) were randomized into four treatment groups. IGF-1 levels were measured at baseline and after 6 weeks of treatment by immunoenzymometric assay as described above. The results are provided at Table 2 below and demonstrate a 35% to 45% reduction in serum IGF-1 levels of subjects treated with trans-clomiphene.

TABLE 2

| Dose | Number of Subjects (n =) | IGF-1 - Naïve men (µg/L) | IGF-1 - Treated men (µg/L) | Compared to AndroGel (MWW) |
|---|---|---|---|---|
| 6.25 mg | 12 | 101 ± 43 | 54 ± 30 | p = 0.008 |
| 12.5 mg | 10 | 94 ± 47 | 50 ± 24 | p = 0.0035 |
| 25 mg | 12 | 96 ± 45 | 62 ± 42 | p = 0.008 |
| AndroGel | 13 | 103 ± 46 | 90 ± 34 | |

Discussion

Together, these results indicate that trans-clomiphene significantly lowers serum IGF-1 levels thereby rendering the SERM useful for treating a variety of cancers in which IGF-1 is strongly expressed or overexpressed. Without being bound by theory, it is believed that trans-clomiphene suppresses the production of hepatic IGF-1 by an endocrine-dependent mechanism thereby reducing the concentration of circulating serum IGF-1.

EXAMPLE 2

Treating Cancer with Antiestrogens

Subjects with cancer may be treated by a protocol similar to that reported in Example 1. In this case, free circulating IGF-1 levels would be established prior to drug treatment and then monitored through the course of treatment. The drug could be trans-clomiphene, or it could be any of the antiestrogenic analogs of trans-clomiphene or a combination of various antiestrogens including trans-clomiphene. In contrast to Example 1 drug treatment would continue until circulating IGF-1 levels were determined to reach normal and stable levels or the cancer was treated.

EXAMPLE 3

Improving Anti-IGF-R Antibody Treatment of Cancer with Antiestrogens

Subjects with cancer undergoing treatment with anti-IGF-R antibodies such as figitumumab may benefit from prior or simultaneous treatment with trans-clomiphene or other antiestrogens to reduce free circulating IGF-1. In this case, free circulating IGF-1 levels would be established prior to antiestrogen treatment. If high levels of IGF-1 are detected, indicating that the subject was unlikely to respond positively to antibody therapy, the subject would be treated with trans-clomiphene or another antiestrogen to reduce circulating IGF-1. Once the IGF-1 level is reduced to an acceptable level, therapeutic antibody treatment would commence.

EXAMPLE 4

Improving IGF-R Tyrosine Kinase Inhibitor Treatment of Cancer with Antiestrogens Subjects with cancer undergoing treatment with tyrosine kinase inhibitors effective against IGF-R may benefit from prior or simultaneous treatment with trans-clomiphene or other antiestrogens to reduce circulating IGF-1. In this case, free circulating IGF-1 levels would be suppressed prior to, or concomitant with, treatment with tyrosine kinase inhibitors effective against IGF-R.

EXAMPLE 5

Improving Efficacy of IGF-BP Treatment of Cancer with Antiestrogens

Subjects with cancer undergoing treatment with IGF-BPs to reduce the level of free circulating IGF-1 may benefit from prior or simultaneous treatment with trans-clomiphene or other antiestrogens to reduce production of circulating IGF-1. In this case, free circulating IGF-1 levels would be suppressed prior to, or concomitant with, treatment with IGF-BP.

EXAMPLE 6

Improving Efficacy of IGF-ASO Treatment of Cancer with Antiestrogens

Subjects with cancer undergoing treatment with IGF-ASOs to reduce the amount of IGF-R present on tumor cells may benefit from prior or simultaneous treatment with trans-clomiphene or other antiestrogens to reduce production of circulating IGF-1. In this case, free circulating IGF-1 levels would be suppressed prior to, or concomitant with, treatment with IGF-ASOs.

The invention claimed is:

1. A method for reducing the level of insulin-like growth factor-1 (IGF-1) in the serum of a human male with cancer and an elevated serum level of IGF-1 relative to a normal range of IGF-1 in an age-matched human male comprising administering to the human male with cancer and an elevated serum level of IGF-1 a composition comprising about 0% cis-clomiphene and about 100% trans-clomiphene or a pharmaceutically acceptable salt or analog thereof and a suitable carrier in an amount effective to reduce IGF-1 levels in the male by at least 30%, wherein the analog of trans-clomiphene is selected from the group consisting of: (E)-4-OH-clomiphene, (E)-4-OH—N-desethyl clomiphene and a pharmaceutically acceptable salt thereof.

2. The method of claim 1, wherein the composition comprises about 5 to 100 mg trans-clomiphene.

3. The method of claim 2, wherein the composition comprises between 6.25 mg and 25 mg trans-clomiphene.

4. The method of claim 1 wherein the composition is administered daily.

5. The method of claim 4 wherein the composition is administered for a period of at least two weeks.

6. The method of claim 1, wherein the IGF-1 level of the human male is above 500 ng/ml.

7. The method of claim 1 wherein the composition is administered in an amount effective to reduce the IGF-1 level of the human male by at least 40%.

8. The method of claim 1, wherein the cancer is lung, hepatocellular, renal, gastrointestinal, osterosarcoma, breast or bladder cancer.

9. The method of claim 1, comprising co-administering with the composition one or more chemotherapeutic agents.

10. The method of claim 9 wherein the one or more chemotherapeutic agents are selected from the group consisting of: an anti-IGF receptor antibody, an IGF receptor-associated kinase inhibitor, an IGF-binding protein and an IGF receptor antisense oligonucleotide.

11. The method of claim 9 wherein the composition and the one or more chemotherapeutic agents are administered sequentially.

12. The method of claim 9 wherein the composition and the one or more chemotherapeutic agents are administered simultaneously.

13. The method of claim 1 wherein the composition comprises an analog of trans-clomiphene selected from the group consisting of: (E)-4-OH-clomiphene and (E)-4-OH—N-desethyl clomiphene or a pharmaceutically acceptable salt thereof.

14. The method of claim 1 wherein the pharmaceutically acceptable salt is the citrate salt.

15. The method of claim 1, wherein the IGF-1 level in human male is above 200 µg/L.

16. The method of claim 1, wherein the IGF-1 level in the human male is above 300 µg/L.

17. The method of claim 1, wherein the human male has a body mass index of at least 30.

18. The method of claim 1, wherein the human male has a total testosterone blood level below 300 ng/dl and a serum LH of less than 15 IU/ml.

* * * * *